US012691121B2

(12) United States Patent
Zhao et al.

(10) Patent No.: US 12,691,121 B2
(45) Date of Patent: Jul. 28, 2026

(54) TREATMENT OF PULMONARY ARTERIAL HYPERTENSION

(71) Applicant: IMPERIAL COLLEGE INNOVATIONS LIMITED, South Kensington (GB)

(72) Inventors: Lan Zhao, South Kensington (GB); David Owen, South Kensington (GB); Martin Wilkins, South Kensington (GB)

(73) Assignee: Imperial College Innovations Limited, London (GB)

(*) Notice: Subject to any disclaimer, the term of this patent is extended or adjusted under 35 U.S.C. 154(b) by 497 days.

(21) Appl. No.: 18/252,002

(22) PCT Filed: Nov. 9, 2021

(86) PCT No.: PCT/GB2021/052895
§ 371 (c)(1),
(2) Date: May 5, 2023

(87) PCT Pub. No.: WO2022/096901
PCT Pub. Date: May 12, 2022

(65) Prior Publication Data

US 2024/0009200 A1 Jan. 11, 2024

(30) Foreign Application Priority Data

Nov. 9, 2020 (GB) ..................................... 2017673

(51) Int. Cl.
*A61K 31/522* (2006.01)
*A61P 9/12* (2006.01)

(52) U.S. Cl.
CPC .............. *A61K 31/522* (2013.01); *A61P 9/12* (2018.01)

(58) Field of Classification Search
CPC .... A61K 31/522; A61K 31/44; A61K 31/472; A61K 31/536; A61K 31/5513; A61P 9/00; A61P 9/12
See application file for complete search history.

(56) References Cited

FOREIGN PATENT DOCUMENTS

| | | | |
|---|---|---|---|
| WO | 2000/037086 | A1 | 6/2000 |
| WO | 2009/137465 | A2 | 11/2009 |

OTHER PUBLICATIONS

Search Report in GB 2017673.1, mailed Apr. 30, 2021, 4 pages.
International Search Report in PCT/GB2021/052895, mailed Feb. 10, 2022, 18 pages.
Evgenov, et al. "Inhibition of phosphodiesterase 1 augments the pulmonary vasodilator response to inhaled nitric oxide in awake lambs with acute pulmonary hypertension." American Journal of Physiology-Lung Cellular and Molecular Physiology 290, No. 4 (2006): L723-L729.
Hatori, et al. "PET imaging of lung inflammation with [18F] FEDAC, a radioligand for translocator protein (18 kDa)." (2012): e45065.
Nevzorova, et al. "The state of cerebral blood flow in hypertensive crises and possibilities of its correction." Kardiologiia 47, No. 12 (2007): 20-23.
Thai, et al. "Cardiac-specific conditional knockout of the 18-kDa mitochondrial translocator protein protects from pressure overload induced heart failure." Scientific reports 8, No. 1 (2018): 16213.
Tsamatsoulis, et al. "Cardioprotective effects of intracoronary administration of 4-chlorodiazepam in small and large animal models of ischemia-reperfusion." International journal of cardiology 224 (2016): 90-95.

*Primary Examiner* — Kevin E Weddington
(74) *Attorney, Agent, or Firm* — Kilpatrick Townsend & Stockton LLP

(57) ABSTRACT

The invention generally relates to products for use in the treatment and/or prevention of Pulmonary Arterial Hypertension (PAH). More specifically, the invention relates to translocator protein (TSPO) binding members which treat or prevent pulmonary endothelial cell dysfunction, and the use of such TSPO binding members for use in the treatment and/or prevention of PAH.

26 Claims, 14 Drawing Sheets

Specification includes a Sequence Listing.

A

B ROS

C Mitochondrial membrane potential

SEQUENCE LISTING

```
<160> NUMBER OF SEQ ID NOS: 2

<210> SEQ ID NO 1
<211> LENGTH: 169
<212> TYPE: PRT
<213> ORGANISM: Homo sapiens

<400> SEQUENCE: 1

Met Ala Pro Pro Trp Val Pro Ala Met Gly Phe Thr Leu Ala Pro Ser
1               5                   10                  15

Leu Gly Cys Phe Val Gly Ser Arg Phe Val His Gly Glu Gly Leu Arg
            20                  25                  30

Trp Tyr Ala Gly Leu Gln Lys Pro Ser Trp His Pro Pro His Trp Val
        35                  40                  45

Leu Gly Pro Val Trp Gly Thr Leu Tyr Ser Ala Met Gly Tyr Gly Ser
    50                  55                  60

Tyr Leu Val Trp Lys Glu Leu Gly Gly Phe Thr Glu Lys Ala Val Val
```

-continued

```
65                  70                  75                  80

Pro Leu Gly Leu Tyr Thr Gly Gln Leu Ala Leu Asn Trp Ala Trp Pro
                85                  90                  95

Pro Ile Phe Phe Gly Ala Arg Gln Met Gly Trp Ala Leu Val Asp Leu
            100                 105                 110

Leu Leu Val Ser Gly Ala Ala Ala Ala Thr Thr Val Ala Trp Tyr Gln
        115                 120                 125

Val Ser Pro Leu Ala Ala Arg Leu Leu Tyr Pro Tyr Leu Ala Trp Leu
    130                 135                 140

Ala Phe Thr Thr Thr Leu Asn Tyr Cys Val Trp Arg Asp Asn His Gly
145                 150                 155                 160

Trp Arg Gly Gly Arg Arg Leu Pro Glu
                165


<210> SEQ ID NO 2
<211> LENGTH: 836
<212> TYPE: DNA
<213> ORGANISM: Homo sapiens

<400> SEQUENCE: 2

aactcctgcc aggcagtgcc cttcccggag cgtgccctcg ccgctgagct cccctgaaca      60

gcagctgcag cagccatggc cccgccctgg gtgcccgcca tgggcttcac gctggcgccc     120

agcctggggt gcttcgtggg ctcccgcttt gtccacggcg agggtctccg ctggtacgcc     180

ggcctgcaga agccctcgtg gcacccgccc cactgggtgc tgggccctgt ctggggcacg     240

ctctactcag ccatggggta cggctcctac ctggtctgga aagagctggg aggcttcaca     300

gagaaggctg tggttcccct gggcctctac actgggcagc tggccctgaa ctgggcatgg     360

ccccccatct tctttggtgc ccgacaaatg ggctgggcct tggtggatct cctgctggtc     420

agtggggcgg cggcagccac taccgtggcc tggtaccagg tgagcccgct ggccgcccgc     480

ctgctctacc cctacctggc ctggctggcc ttcacgacca cactcaacta ctgcgtatgg     540

cgggacaacc atggctggcg tgggggacgg cggctgccag agtgagtgcc cggcccacca     600

gggactgcag ctgcaccagc aggtgccatc acgcttgtga tgtggtggcc gtcacgcttt     660

catgaccact gggcctgcta gtctgtcagg gccttggccc aggggtcagc agagcttcag     720

aggtggcccc acctgagccc ccacccggga gcagtgtcct gtgctttctg catgcttaga     780

gcatgttctt ggaacatgga attttataag ctgaataaag tttttgactt ccttta         836
```

TREATMENT OF PULMONARY ARTERIAL HYPERTENSION

CROSS REFERENCE TO RELATED APPLICATIONS

This application is a U.S. National Stage of PCT/GB2021/052895, international filing date Nov. 9, 2021, which claims priority to GB2017673.1, filing date Nov. 9, 2020, the disclosures of all of which are incorporated herein by reference for all purposes.

REFERENCE TO SUBMISSION OF A SEQUENCE LISTING AS A TEXT FILE

The Sequence Listing written in file Sequence-Listing-1386802.txt created on May 2, 2023, 8,192 bytes, machine format IBM-PC, MS-Windows operating system, is hereby incorporated by reference in its entirety for all purposes.

FIELD OF THE INVENTION

The invention generally relates to products for use in the treatment and/or prevention of Pulmonary Arterial Hypertension (PAH). More specifically, the invention relates to translocator protein (TSPO) binding members which treat or prevent pulmonary endothelial cell dysfunction, and the use of such TSPO binding members for use in the treatment and/or prevention of PAH.

BACKGROUND OF THE INVENTION

Pulmonary Hypertension (PH) is a fatal disease characterized by lung blood vessel obstruction due to excessive proliferation of vascular cells (endothelial cells, smooth muscle cells and fibroblasts) and inflammation. Similar to the Warburg effect in cancer, a shift from mitochondrial oxidation to glycolysis occurs in diseased pulmonary vessels, the infiltrated inflammatory cells and the right ventricle, as well as other molecular, translational and clinical concepts centred on the mitochondria, leading to chronic elevation of pulmonary artery pressure. The increased pulmonary pressure causes hypertrophy of the right heart and eventually failure.

PH is currently classified into five separate groups with distinct pathophysiological characteristics. Rare forms include pulmonary arterial hypertension (PAH, Group 1) and PH due to pulmonary artery obstructions (Group 4, primarily chronic thromboembolic PH [CTEPH]). More common forms include usually mild elevations of pressure seen in significant cardiac (PH due to left heart disease, Group 2) and respiratory disease (PH due to lung diseases and/or hypoxia, Group 3) and PH with unclear and/or multifactorial mechanisms (Group 5).

The most common symptoms of PAH are progressive breathlessness, fatigue, syncope, and clinical signs of heart failure. The mechanisms underlying PAH are complex, with multiple genetic, epigenetic and environmental mechanisms resulting in remodelling of the pulmonary vasculature.

Pulmonary vascular remodelling in PAH involves medial hypertrophy/hyperplasia, intimal and adventitial fibrosis, (in situ) thrombotic lesions, and plexiform lesions, as well as perivascular infiltration of inflammatory cells (B- and T-lymphocytes, mast cells, dendritic cells, macrophages, etc.). It affects mainly distal muscular-type pulmonary arterial vessels and small pre-capillary arterioles, but post-capillary veins and bronchial arteries are also affected.

Multiple cell types, including pulmonary arterial endothelial cells, fibroblasts, pulmonary arterial smooth muscle cells, myofibroblasts and pericytes are involved in the process of pulmonary vascular remodelling. Remodelling can be trigged by multiple factors, including trauma, environmental factors such as air pollution and smoke exposure, and can be exacerbated by genetic/epigenetic susceptibility. PAH can also be promoted by circulating factors such as hormones and metabolites.

Previously, understanding and treating PAH has been hampered by the multifactorial nature of the disease. There have been recent advances in both understanding of PH, including PAH, with new treatments targeting the prostacyclin, endothelin and NO pathways. However, despite these advances, prognosis of PH, particularly PAH, remains poor. The treatment options in use are typically based on relaxing vascular tone rather than halting or reversing the underlying disease. There is therefore an urgent need for effective treatments that tackle the underlying disease mechanisms—inflammation, glycolytic metabolism and aberrant vascular cell proliferation. It is an object of the present invention to addresses these challenges and to provide a safe and effective treatment for PAH which targets the underlying mechanisms of the disease.

SUMMARY OF THE INVENTION

The present inventors have previously shown that expression of translocator protein (TSPO) is increased in the pulmonary vessels of patients with idiopathic PAH (IPAH), and also in the pulmonary vessels of a rat model of PH (monocrotaline (MCT)-induced PH). The inventors have surprisingly shown for the first time that treatment of MCT rats with XBD173 (a binding member for TSPO) attenuates the PH phenotype without affecting systemic blood pressure, and that this can be achieved using doses of XBD-173 comparable to the licensed dose for humans. In particular, the inventors have shown that treatment with XBD173 reduces pulmonary arterial pressure (PAP) and pulmonary vascular remodelling. The inventors have also shown that XBD173 treatment reduces remodelling of the right ventricle (RV) and improves cardiac performance, and attenuates glucose uptake in both lung and RV. Further, the inventors have demonstrated that in vitro XBD173 treatment inhibits DMOG (a permeable prolyl-4-hydroxylase inhibitor which upregulates hypoxia-inducible factor) induced endothelial apoptosis, and PDGF- and hypoxia-induced pulmonary smooth muscle cell proliferation. Thus, the inventors have demonstrated for the first time that targeting TSPO has therapeutic potential in the treatment of PH, particularly PAH, providing a disease modifying strategy as opposed to the conventional approach which essentially vasorelaxes blood vessels.

Accordingly, the present invention provides a translocator protein (TSPO) modulator for use in a method of treating or preventing pulmonary endothelial cell (PEC) dysfunction.

The TSPO modulator may inhibit pro-inflammatory activation of pulmonary endothelial cells. Inhibition of pro-inflammatory activation of pulmonary endothelial cells may comprise: (a) reducing or attenuating an increase in expression of E-selectin, ICAM1 and/or VCAM1 by said pulmonary endothelial cells; and/or (b) modulating (preferably reducing) the level of one or more pro-inflammatory mediator, wherein optionally said one or more pro-inflammatory mediator is selected from IFN-gamma; IL1, 2, 6, 8, 10, 17, 18 or 21; IP10 (CXCL10); I-TAC (CXCL11); G-CSF; MCP-1; PAI1, TNF-alpha, RANTES and/or SDF-1 (CXCL12).

The TSPO modulator may: (a) reduce or attenuate an increase in pulmonary endothelial cell apoptosis; (b) reduce or attenuate an increase in reactive oxygen species (ROS) production by said PECs; (c) reduce or attenuate an increase in vascular tone; (d) reverse the active metabolic changes seen in pulmonary endothelial cell dysfunction; (e) increase or attenuate a decrease in anticoagulant properties (particularly of PECs); (f) increase or attenuate a decrease in vascular tubule formation; (g) increase or attenuate a decrease in vascular repair; (h) reduce or attenuate an increase in disordered pulmonary endothelial cell proliferation and associated neoangiogenesis; (i) increase or attenuate a decrease in mitochondrial membrane potential; and/or (j) reduce or attenuate an increase in expression of markers of endothelial to mesenchymal transition in PECs. The TSPO modulator may reduce hypoxia-induced pulmonary endothelial cell proliferation by at least 30%, preferably at least 40%.

The TSPO modulator may: (a) reduce or attenuate an increase in pulmonary arterial pressure; (b) reduce or attenuate an increase in pulmonary vascular remodelling; (c) reduce or attenuate an increase in infiltration of inflammatory cells, particularly CD68+ cells, into the lungs; and/or (d) reduce or attenuate an increase in glucose uptake in the lung. The TSPO modulator may reduce pulmonary arterial pressure by at least 30%, preferably by at least 40%. Pulmonary vascular remodelling may correspond with the percentage of smooth muscle cells within the pulmonary vasculature. The TSPO modulator may reduce the percentage of smooth muscle cells within the pulmonary vasculature by at least 30%, preferably at least 40%. The TSPO modulator may reduce the infiltration of inflammatory cells, particularly $CD68^+$ cells, into the pulmonary vasculature and/or lung tissue by at least 30%, preferably at least 40%. The TSPO modulator may reduce glucose uptake by the pulmonary endothelial cells of at least 40%, preferably at least 50%.

The dysfunction of the pulmonary endothelial cells may be associated with: (a) pulmonary hypertension; and/or (b) heart failure. The pulmonary hypertension may be pulmonary arterial hypertension (PAH), optionally idiopathic pulmonary arterial hypertension (IPAH). The heart failure may be heart failure with preserved ejection fraction and associated pulmonary hypertension (PH-HFpEF).

The TSPO modulator may: (a) reduce or attenuate an increase in right ventricular systolic pressure; (b) reduce or attenuate an increase in right ventricular hypertrophy, particularly cardiomyocyte hypertrophy in the right ventricle; (c) reduce or attenuate an increase in glucose uptake in the right ventricle; (d) reduce or attenuate an increase in remodelling of the right ventricle; (e) increase capillary density within the cardiac tissue; and/or (f) improve cardiac performance.

The TSPO modulator typically has no effect on systemic blood pressure.

The TSPO modulator may preferably be a TSPO binding member. A TSPO binding member may be selected from a small molecule, an antibody or antigen-binding fragment thereof, a peptide, a peptidomimetic, a nucleic acid or an aptamer, wherein preferably the TSPO binding member is a small molecule. The TSPO modulator may be a TSPO binding member selected from XBD-173, ONO-2952, PK11195, PBR28, DPA713, DPA714, Ro 5-4864, FGIN-1-27, diazepam, lorazepam, midazolam, vinpocetine, etifoxine, or a derivative or analogue thereof, optionally in the form of a pharmaceutically acceptable salt. In some embodiments, the TSPO modulator is not vinpocetine, or is a TSPO binding member that is not vinpocetine. Thus, the TSPO modulator may be a TSPO binding member selected from XBD-173, ONO-2952, PK11195, PBR28, DPA713, DPA714, Ro 5-4864, FGIN-1-27, diazepam, lorazepam, midazolam, etifoxine, or a derivative or analogue thereof, optionally in the form of a pharmaceutically acceptable salt.

The TSPO modulator may be comprised within a pharmaceutical composition. The TSPO modulator may be administered by oral administration, intravenous or intra-arterial administration or by inhalation.

In some preferred embodiments the TSPO modulator is the TSPO binding member XBD-173 and the pulmonary endothelial cell dysfunction is associated with pulmonary arterial hypertension, particularly idiopathic pulmonary arterial hypertension.

The invention further provides a method for treating or preventing pulmonary endothelial cell dysfunction, the method comprising administering a therapeutically effective amount of a TSPO modulator.

The invention also provides the use of a TSPO modulator in the manufacture of a medicament for use in the treatment or prevention of pulmonary endothelial cell dysfunction.

DETAILED DESCRIPTION OF THE INVENTION

Definitions

Figure 1:
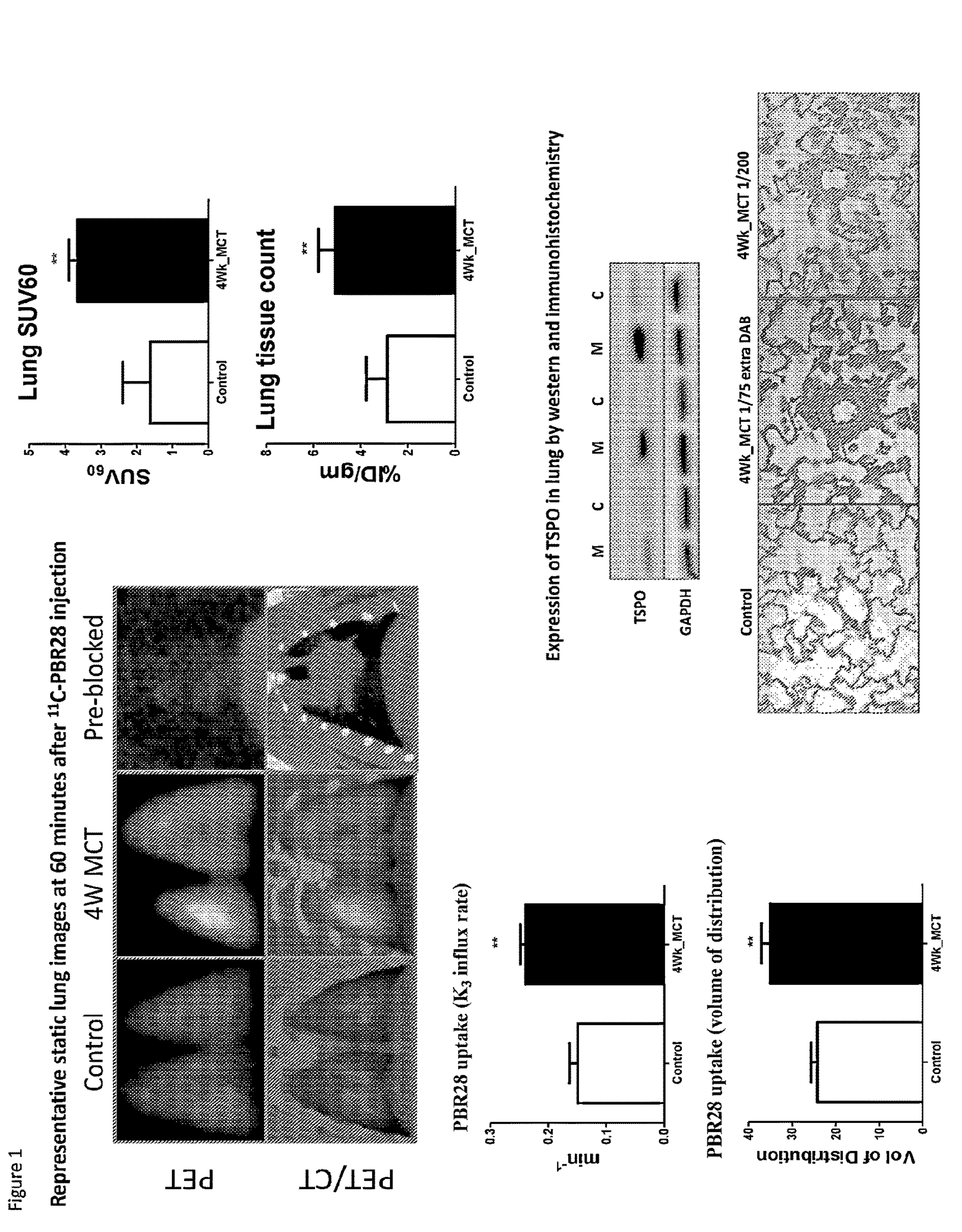
FIG. 1: PBR28 uptake in the lung. Representative static images (PET/CT co-registered) of the lungs at 60 minutes after $^{11}$C-PBR28 injection and bar charts for $^{11}$C-PBR28 lung uptake (expressed as standardized uptake value (SUV) and lung tissue counts (percentage of injected dose, % ID) demonstrated a two-fold increase of PBR28 in the lung, representing the increased receptor biding. XBD-173 prior treatment blocked PBR28 lung signals, confirming the radioligand specificity. **$p<0.01$ compared with control.

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide the skilled person with a general dictionary of many of the terms used in this disclosure. The meaning and scope of the terms should be clear; however, in the event of any latent ambiguity, definitions provided herein take precedent over any dictionary or extrinsic definition. It should be understood that this invention is not limited to the particular methodology, protocols, and reagents, etc., described herein and as such can vary.

This disclosure is not limited by the exemplary methods and materials disclosed herein, and any methods and materials similar or equivalent to those described herein can be used in the practice or testing of embodiments of this disclosure. The terminology used herein is for the purpose of describing particular embodiments only, and is not intended to limit the scope of the present invention, which is defined solely by the claims.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure.

As used herein, the term "capable of" when used with a verb, encompasses or means the action of the corresponding verb. For example, "capable of interacting" also means interacting, "capable of cleaving" also means cleaves, "capable of binding" also means binds and "capable of specifically targeting . . . " also means specifically targets.

Other definitions of terms may appear throughout the specification. Before the exemplary embodiments are described in more detail, it is to be understood that this disclosure is not limited to particular embodiments described, and as such may vary. It is also to be understood that the terminology used herein is for the purpose of describing particular embodiments only, and is not intended to be limiting, since the scope of the present disclosure will be defined only by the appended claims.

Numeric ranges are inclusive of the numbers defining the range. Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

As used herein, the articles "a" and "an" may refer to one or to more than one (e.g. to at least one) of the grammatical object of the article. Further, unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting.

"About" may generally mean an acceptable degree of error for the quantity measured given the nature or precision of the measurements. Exemplary degrees of error are within 20 percent (%), typically, within 10%, and more typically, within 5% of a given value or range of values. Preferably, the term "about" shall be understood herein as plus or minus (±) 5%, preferably ±4%, ±3%, ±2%, ±1%, ±0.5%, ±0.1%, of the numerical value of the number with which it is being used.

The term "consisting of" refers to compositions, methods, and respective components thereof as described herein, which are exclusive of any element not recited in that description of the invention.

As used herein the term "consisting essentially of" refers to those elements required for a given invention. The term permits the presence of elements that do not materially affect the basic and novel or functional characteristic(s) of that invention (i.e. inactive or non-immunogenic ingredients).

Embodiments described herein as "comprising" one or more features may also be considered as disclosure of the corresponding embodiments "consisting of" and/or "consisting essentially of" such features.

Concentrations, amounts, volumes, percentages and other numerical values may be presented herein in a range format. It is also to be understood that such range format is used merely for convenience and brevity and should be interpreted flexibly to include not only the numerical values explicitly recited as the limits of the range but also to include all the individual numerical values or sub-ranges encompassed within that range as if each numerical value and sub-range is explicitly recited.

Amino acids are referred to herein using the name of the amino acid, the three-letter abbreviation or the single letter abbreviation.

As used herein, the terms "protein" and "polypeptide" are used interchangeably herein to designate a series of amino acid residues, connected to each other by peptide bonds between the alpha-amino and carboxyl groups of adjacent residues. The terms "protein", and "polypeptide" refer to a polymer of amino acids, including modified amino acids (e.g., phosphorylated, glycated, glycosylated, etc.) and amino acid analogues, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogues of the foregoing.

Minor variations in the amino acid sequences of proteins of the invention are contemplated as being encompassed by the present invention, providing that the variations in the amino acid sequence(s) maintain at least 60%, at least 70%, more preferably at least 80%, at least 85%, at least 90%, at least 95%, and most preferably at least 97% or at least 99% sequence identity to the proteins of the invention or an immunogenic fragment thereof as defined anywhere herein. The term homology is used herein to mean identity. As such, the sequence of a variant or analogue sequence of a protein of the invention may differ on the basis of substitution (typically conservative substitution) deletion or insertion.

Proteins of the invention may include variants in which amino acid residues from one species are substituted for the corresponding residue in another species, either at the conserved or non-conserved positions. Variants of protein molecules disclosed herein may be produced and used in the present invention. Following the lead of computational chemistry in applying multivariate data analysis techniques to the structure/property-activity relationships [see for example, Wold, et al. Multivariate data analysis in chemistry. Chemometrics-Mathematics and Statistics in Chemistry (Ed.: B. Kowalski); D. Reidel Publishing Company, Dordrecht, Holland, 1984 (ISBN 90-277-1846-6] quantitative activity-property relationships of proteins can be derived using well-known mathematical techniques, such as statistical regression, pattern recognition and classification [see for example Norman et al. Applied Regression Analysis. Wiley-Interscience; 3rd edition (April 1998) ISBN: 0471170828; Kandel, Abraham et al. Computer-Assisted Reasoning in Cluster Analysis. Prentice Hall PTR, (May 11, 1995), ISBN: 0133418847; Krzanowski, Wojtek. Principles of Multivariate Analysis: A User's Perspective (Oxford Statistical Science Series, No 22 (Paper)). Oxford University Press; (December 2000), ISBN: 0198507089; Witten, Ian H. et al Data Mining: Practical Machine Learning Tools and Techniques with Java Implementations. Morgan Kaufmann; (Oct. 11, 1999), ISBN:1558605525; Denison David G. T. (Editor) et al Bayesian Methods for Nonlinear Classification and Regression (Wiley Series in Probability and Statistics). John Wiley & Sons; (July 2002), ISBN: 0471490369; Ghose, Arup K. et al. Combinatorial Library Design and Evaluation Principles, Software, Tools, and Applications in Drug Discovery. ISBN: 0-8247-0487-8]. The properties of proteins can be derived from empirical and theoretical models (for example, analysis of likely contact residues or calculated physicochemical property) of proteins sequence, functional and three-dimensional structures and these properties can be considered individually and in combination.

Amino acids are referred to herein using the name of the amino acid, the three-letter abbreviation or the single letter abbreviation. The term "protein", as used herein, includes proteins, polypeptides, and peptides. As used herein, the term "amino acid sequence" is synonymous with the term "polypeptide" and/or the term "protein". In some instances, the term "amino acid sequence" is synonymous with the term "peptide". The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Amino acid residues at non-conserved positions may be substituted with conservative or non-conservative residues. In particular, conservative amino acid replacements are contemplated.

A "conservative amino acid substitution" is one in which the amino acid residue is replaced with an amino acid residue having a similar side chain. Families of amino acid residues having similar side chains have been defined in the art, including basic side chains (e.g., lysine, arginine, or histidine), acidic side chains (e.g., aspartic acid or glutamic acid), uncharged polar side chains (e.g., glycine, asparagine, glutamine, serine, threonine, tyrosine, or cysteine), nonpolar side chains (e.g., alanine, valine, leucine, isoleucine, proline, phenylalanine, methionine, or tryptophan), beta-branched side chains (e.g., threonine, valine, isoleucine) and aromatic side chains (e.g., tyrosine, phenylalanine, tryptophan, or histidine). Thus, if an amino acid in a polypeptide is replaced with another amino acid from the same side chain family, the amino acid substitution is considered to be conservative. The inclusion of conservatively modified variants in a protein of the invention does not exclude other forms of variant, for example polymorphic variants, interspecies homologs, and alleles.

"Non-conservative amino acid substitutions" include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, His, Ile or Trp) is substituted for, or by, one having a smaller side chain (e.g., Ala or Ser) or no side chain (e.g., Gly).

"Insertions" or "deletions" are typically in the range of about 1, 2, or 3 amino acids. The variation allowed may be experimentally determined by systematically introducing insertions or deletions of amino acids in a protein using recombinant DNA techniques and assaying the resulting recombinant variants for activity. This does not require more than routine experiments for a skilled person.

A "fragment" of a polypeptide comprises at least 50%, at least 60%, at least 70%, at least 80%, at least 90%, at least 95%, at least 97% or more of the original polypeptide.

The proteins of the invention, or immunogenic fragments thereof, include both intact and modified forms of the proteins disclosed herein. For example, a protein of the invention or immunogenic fragment thereof can be functionally linked (e.g. by chemical coupling, genetic fusion, noncovalent association, or otherwise) to one or more other molecular entities, such as a pharmaceutical agent, a detection agent, and/or a protein or peptide that can mediate association of a binding molecule disclosed herein with another molecule (e.g. a streptavidin core region or a polyhistidine tag). Non-limiting examples of detection agents include: enzymes, such as alkaline phosphatase, glucose-6-phosphate dehydrogenase ("G6PDH"), alpha-D-galactosidase, glucose oxydase, glucose amylase, carbonic anhydrase, acetylcholinesterase, lysozyme, malate dehydrogenase and peroxidase, e.g., horseradish peroxidase; dyes; fluorescent labels or fluorescers, such as fluorescein and its derivatives, fluorochrome, rhodamine compounds and derivatives, GFP (GFP for "Green Fluorescent Protein"), dansyl, umbelliferone, phycoerythrin, phycocyanin, allophycocyanin, o-phthaldehyde, and fluorescamine; fluorophores such as lanthanide cryptates and chelates, e.g., Europium etc., (Perkin Elmer and Cis Biointernational); chemoluminescent labels or chemiluminescers, such as isoluminol, luminol and the dioxetanes; bio-luminescent labels, such as luciferase and luciferin; sensitizers; coenzymes; enzyme substrates; radiolabels, including but not limited to, bromine$^{77}$, carbon$^{14}$, cobalt$^{57}$, fluorine$^{8}$, gallium$^{67}$, gallium$^{68}$, hydrogen$^{3}$ (tritium), indium$^{111}$, indium$^{113m}$, iodine$^{123m}$, iodine125, iodine$^{126}$, iodine$^{131}$, iodine$^{133}$, mercury$^{107}$, mercury$^{203}$, phosphorous$^{32}$, rhenium$^{99m}$, rhenium$^{101}$, rhenium$^{105}$, ruthenium$^{95}$, ruthenium$^{97}$, ruthenium$^{103}$, ruthenium$^{105}$, scandium$^{47}$, selenium$^{75}$, sulphur$^{35}$, technetium$^{99}$, technetium$^{99m}$, tellurium$^{121m}$, tellurium$^{122m}$, tellurium$^{125m}$, thulium$^{165}$, thulium$^{167}$, thulium$^{168}$ and yttrium$^{199}$; particles, such as latex or carbon particles, metal sol, crystallite, liposomes, cells, etc., which may be further labelled with a dye, catalyst or other detectable group; molecules such as biotin, digoxygenin or 5-bromodeoxyuridine; toxin moieties, such as for example a toxin moiety selected from a group of *Pseudomonas* exotoxin (PE or a cytotoxic fragment or mutant thereof), Diptheria toxin or a cytotoxic fragment or mutant thereof, a Botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

The proteins of the invention or immunogenic fragments thereof also include derivatives that are modified (e.g., by the covalent attachment of any type of molecule to the protein) such that covalent attachment does not prevent the protein from binding to antibodies specific for said protein, or otherwise impair the biological activity of the protein. Examples of suitable derivatives include, but are not limited to fucosylated proteins, glycosylated proteins, acetylated proteins, PEGylated proteins, phosphorylated proteins, and amidated proteins.

A typical antibody comprises at least two "light chains" (LC) and two "heavy chains" (HC). The light chains and heavy chains of such antibodies are polypeptides consisting of several domains. Each heavy chain comprises a heavy chain variable region (abbreviated herein as "VH") and a heavy chain constant region (abbreviated herein as "CH"). The heavy chain constant region comprises the heavy chain constant domains CH1, CH2 and CH3 (antibody classes IgA, IgD, and IgG) and optionally the heavy chain constant domain CH4 (antibody classes IgE and IgM). Each light chain comprises a light chain variable domain (abbreviated herein as "VL") and a light chain constant domain (abbreviated herein as "CL"). The variable regions VH and VL can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The "constant domains" of the heavy chain and of the light chain are not involved directly in binding of an antibody to a target, but exhibit various effector functions.

Binding between an antibody and its target antigen or epitope is mediated by the Complementarity Determining Regions (CDRs). The CDRs are regions of high sequence variability, located within the variable region of the antibody heavy chain and light chain, where they form the antigen-binding site. The CDRs are the main determinants of antigen specificity. Typically, the antibody heavy chain and light chain each comprise three CDRs which are arranged non-consecutively. The antibody heavy and light chain CDR3 regions play a particularly important role in the binding specificity/affinity of the antibodies according to the invention and therefore provide a further aspect of the invention.

Thus, the term "antigen binding fragment" as used herein incudes any naturally-occurring or artificially-constructed configuration of an antigen-binding polypeptide comprising one, two or three light chain CDRs, and/or one, two or three heavy chain CDRs, wherein the polypeptide is capable of binding to the antigen.

The sequence of a CDR may be identified by reference to any number system known in the art, for example, the Kabat system (Kabat, E. A., et al., Sequences of Proteins of Immunological Interest, 5th ed., Public Health Service, National Institutes of Health, Bethesda, MD (1991); the Chothia system (Chothia &, Lesk, "Canonical Structures for the Hypervariable Regions of Immunoglobulins," J. Mol. Biol. 196, 901-917 (1987)); or the IMGT system (Lefranc et al., "IMGT Unique Numbering for Immunoglobulin and Cell Receptor Variable Domains and Ig superfamily V-like domains," Dev. Comp. Immunol. 27, 55-77 (2003)).

For heavy chain constant region amino acid positions discussed in the invention, numbering is according to the EU index first described in Edelman, G. M., et al., Proc. Natl. Acad. Sci. USA 63 (1969) 78-85). The EU numbering of Edelman is also set forth in Kabat et al. (1991) (supra.). Thus, the terms "EU index as set forth in Kabat", "EU Index". "EU index of Kabat" or "EU numbering" in the context of the heavy chain refers to the residue numbering system based on the human IgG1 EU antibody of Edelman et al. as set forth in Kabat et al. (1991). The numbering system used for the light chain constant region amino acid sequence is similarly set forth in Kabat et al. (supra.). Thus, as used herein, "numbered according to Kabat" refers to the Kabat numbering system set forth in Kabat et al. (supra.).

The antibodies of the invention or antigen-binding fragments thereof are preferably monoclonal antibodies. More preferably, the antibodies of the invention or antigen-binding fragments thereof are isolated monoclonal antibodies.

The term "humanized antibody" refers to antibodies in which the framework or "complementarity determining regions" (CDRs) have been modified to comprise the CDR of an immunoglobulin of different specificity as compared to that of the parent immunoglobulin. For example, a murine CDR may be grafted into the framework region of a human antibody to prepare the "humanized antibody." See, e.g., Riechmann, L., et al., Nature 332 (1988) 323-327; and Neuberger, M. S., et al., Nature 314 (1985) 268-270. In some embodiments, "humanized antibodies" are those in which the constant region has been additionally modified or changed from that of the original antibody to generate the properties of the antibodies according to the invention, especially in regard to Clq binding and/or Fc receptor (FcR) binding.

The term "chimeric antibody" refers to an antibody comprising a variable region, i.e., binding region, from one source or species and at least a portion of a constant region derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties of the antibodies according to the invention, especially in regard to Clq binding and/or Fc receptor (FcR) binding. Such chimeric antibodies are also referred to as "class-switched antibodies". Chimeric antibodies are the product of expressed immunoglobulin genes comprising DNA segments encoding immunoglobulin variable regions and DNA segments encoding immunoglobulin constant regions. Methods for producing chimeric antibodies involving conventional recombinant DNA and gene transfection techniques are well known in the art. See, e.g., Morrison, S. L., et al., Proc. Natl. Acad. Sci. USA 81 (1984) 6851-6855; U.S. Pat. Nos. 5,202,238 and 5,204,244.

The terms "Fc region", "Fc part" and "Fc" are used interchangeably herein and refer to the portion of a native immunoglobulin that is formed by two Fc chains. Each "Fc chain" comprises a constant domain CH2 and a constant domain CH3. Each Fc chain may also comprise a hinge region. A native Fc region is homodimeric. In some embodiments, the Fc region may be heterodimeric because it may contain modifications to enforce Fc heterodimerization.

There are five major classes of heavy chain constant region, classified as IgA, IgG, IgD, IgE and IgM, each with characteristic effector functions designated by isotype. For example, IgG is separated into four subclasses known as IgGI, IgG2, IgG3, and IgG4. Ig molecules interact with multiple classes of cellular receptors. For example, IgG molecules interact with three classes of Fcγ receptors (FcγR) specific for the IgG class of antibody, namely FcγRI, FcγRII, and FcγRIII. The important sequences for the binding of IgG to the FcγR receptors have been reported to be located in the CH2 and CH3 domains.

The antibodies of the invention or antigen-binding fragments thereof may be any isotype, i.e. IgA, IgD, IgE, IgG and IgM, and synthetic multimers of the four-chain immunoglobulin (Ig) structure.

The terms "Fab fragment" and "Fab" are used interchangeably herein and contain a single light chain (e.g. a constant domain CL and a VL) and a single heavy chain (e.g. the constant domain CH1 and a VH). The heavy chain of a Fab fragment is not capable of forming a disulfide bond with another heavy chain.

A "Fab' fragment" contains a single light chain and a single heavy chain but in addition to the CH1 and the VH, a "Fab' fragment" contains the region of the heavy chain between the CH1 and CH2 domains that is required for the formation of an inter-chain disulfide bond. Thus, two "Fab' fragments" can associate via the formation of a disulphide bond to form a F(ab')2 molecule.

A "F(ab')2 fragment" contains two light chains and two heavy chains. Each chain includes a portion of the constant region necessary for the formation of an inter-chain disulfide bond between two heavy chains.

An "Fv fragment" contains only the variable regions of the heavy and light chain. It contains no constant regions.

A "single-domain antibody" is an antibody fragment containing a single antibody domain unit (e.g., VH or VL).

A "single-chain Fv" ("scFv") is antibody fragment containing the VH and VL domain of an antibody, linked together to form a single chain. A polypeptide linker is commonly used to connect the VH and VL domains of the scFv.

A "tandem scFv", also known as a TandAb®, is a single-chain Fv molecule formed by covalent bonding of two scFvs in a tandem orientation with a flexible peptide linker. A "bi-specific T cell engager" (BiTE®) is a fusion protein consisting of two single-chain variable fragments (scFvs) on a single peptide chain. One of the scFvs binds to T cells via the CD3 receptor, and the other to a tumour cell antigen.

A "diabody" is a small bivalent and bispecific antibody fragment comprising a heavy (VH) chain variable domain connected to a light chain variable domain (VL) on the same polypeptide chain (VH-VL) connected by a peptide linker that is too short to allow pairing between the two domains on the same chain (Kipriyanov, Int. J. Cancer 77 (1998), 763-772). This forces pairing with the complementary domains of another chain and promotes the assembly of a dimeric molecule with two functional antigen binding sites.

The antibodies of the invention or antigen-binding fragments thereof also include derivatives that are modified (e.g., by the covalent attachment of any type of molecule to the antibody) such that covalent attachment does not prevent the antibody from binding to its epitope, or otherwise impair the biological activity of the antibody. Examples of suitable derivatives include, but are not limited to fucosylated antibodies, glycosylated antibodies, acetylated antibodies, PEGylated antibodies, phosphorylated antibodies, and amidated antibodies.

Further embodiments are multispecific antibodies (bispecific, trispecific etc.) and other conjugates, e.g. with cytotoxic small molecules.

As used herein, the terms "polynucleotides", "nucleic acid" and "nucleic acid sequence" refers to any molecule, preferably a polymeric molecule, incorporating units of ribonucleic acid, deoxyribonucleic acid or an analogue thereof. The nucleic acid can be either single-stranded or double-stranded. A single-stranded nucleic acid can be one nucleic acid strand of a denatured double-stranded DNA Alternatively, it can be a single-stranded nucleic acid not derived from any double-stranded DNA. In one aspect, the nucleic acid can be DNA. In another aspect, the nucleic acid can be RNA Suitable nucleic acid molecules are DNA, including genomic DNA or cDNA. Other suitable nucleic acid molecules are RNA, including siRNA, shRNA, and antisense oligonucleotides.

An exemplary, but non-limiting amino acid sequence of human TSPO may comprise or consist of UniProt Accession No. P30536 (version 3 of the sequence, sequence for the entry last modified 30 Nov. 2010, provided herein as SEQ ID NO: 1). The corresponding mRNA sequence is SEQ ID NO: 2.

The terms "decrease", "reduced", "reduction", or "inhibit" are all used herein to mean a decrease by a statistically significant amount. The terms "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" encompasses a complete inhibition or reduction as compared to a reference level. "Complete inhibition" is a 100% inhibition (i.e. abrogation) as compared to a reference level. A decrease can be preferably down to a level accepted as within the range of normal for an individual without a given disorder.

The terms "increased", "increase", "enhance", or "activate" are all used herein to mean an increase by a statically significant amount. The terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a increase, or any increase between 2-fold and 10-fold or greater as compared to a reference level. In the context of a marker or symptom, an "increase" is a statistically significant increase in such level.

References herein to the level of a particular molecule (e.g. TSPO, any of the binding members described herein or a reporter molecule for an outcome of the invention, e.g. glucose) encompass the actual amount of the molecule, such as the mass, molar amount, concentration or molarity of the molecule. Preferably in the context of the invention, references to the level of a particular molecule refer to the concentration of the molecule. References herein to the level of particular cell type (e.g. $CD68^+$ cells and/or pulmonary smooth muscle cells) encompass both the actual number of that cell type or a concentration thereof.

The level of a molecule may be determined in any appropriate physiological compartment. Preferred physiological compartments include bronchoalveolar lavage (BAL), plasma, whole blood and/or serum. The level of a molecule may be determined from any appropriate sample from an individual, e.g. a BAL sample plasma sample, a blood sample and/or a serum sample. Other non-limiting examples of samples which may be tested are tissue or fluid samples, such as urine and biopsy samples. Thus, by way of non-limiting example, the invention may reference the level (e.g. concentration) of a molecule (e.g. TSPO, any of the binding members described herein or a reporter molecule for an outcome of the invention, e.g. glucose) in the BAL and/or plasma of an individual. The level of a molecule pre-treatment with a binding member of the invention may be interchangeably referred to as the "baseline".

The level of a molecule (e.g. TSPO, any of the binding members described herein or a reporter molecule for an outcome of the invention, e.g. glucose) may be compared with any appropriate control. For example, a control may be obtained from a healthy individual or an individual without (clinically relevant) pulmonary endothelial cell dysfunction, particularly PH or PAH, to be treated according to the invention. Alternatively, the control may be obtained from the same individual prior to treatment, or from a different individual with (clinically relevant) pulmonary endothelial cell dysfunction, particularly PH or PAH, but wherein the different individual has not been treated with a binding member of the invention.

The level of a molecule (e.g. TSPO, any of the binding members described herein or a reporter molecule for an outcome of the invention, e.g. glucose) after treatment with an agent of the invention may be compared with the level of the molecule in the individual pre-treatment with the agent. Thus, the invention may be concerned with the relative level of the molecule (e.g. TSPO, any of the binding members described herein or a reporter molecule for an outcome of the invention, e.g. glucose) pre- and post-treatment. The level of a molecule pre-treatment (e.g. TSPO, any of the binding members described herein or a reporter molecule for an outcome of the invention, e.g. glucose) may be used to identify an individual as suitable for treatment according to the invention. Alternatively or in addition, biomarkers for PEC dysfunction/pulmonary hypertension (e.g. pulmonary arterial hypertension, optionally idiopathic PAH)/heart failure such as E-selectin, ICAM1, VCAM1 or N-terminal pro B-type natriuretic peptide (NT-proBNP) could be used to identify an individual as suitable for treatment according to the invention. Other parameters may also be used, either alone or in combination with the level of a molecule as described above, to identify an individual as suitable for treatment according to the invention. Suitable parameters to identify an individual as suitable for treatment according to the invention are known to the skilled person. For example, the presence and/or amount of a biomarker is used to identify an individual as suitable for treatment. The biomarker may, for example, be a circulating protein biomarker. Physiological biomarkers, such as mean pulmonary arterial pressure (mPAP) may also be used. By way of non-limiting example, an individual may be identified as suitable for treatment if they have a mPAP of >20 mmHg. Imaging biomarkers may also be used to identify an individual as suitable for treatment according to the invention. The imaging biomarkers may be identified, for example, through analysis of computerised tomography (CT) images.

The level of a molecule may be measured directly or indirectly, and may be determined using any appropriate technique. Suitable standard techniques are known in the art, for example Western blotting and enzyme-linked immunosorbent assays (ELISAs).

An individual can be one who has been previously diagnosed with or identified as suffering from or having a condition in need of treatment or one or more complications related to such a condition, and optionally, have already undergone treatment for a condition as defined herein or the one or more complications related to said condition. Alternatively, an individual can also be one who has not been previously diagnosed as having a condition as defined herein or one or more complications related to said condition. For example, an individual can be one who exhibits one or more risk factors for a condition, or one or more complications related to said condition or a subject who does not exhibit risk factors.

An "individual in need" of treatment for a particular condition can be an individual having that condition, diagnosed as having that condition, or at risk of developing that condition.

The terms "subject", "individual" and "patient" are used interchangeably herein to refer to a mammalian individual. An "individual" may be any mammal. Generally, the individual may be human; in other words, in one embodiment, the "individual" is a human. A "individual" may be an adult, juvenile or infant. An "individual" may be male or female.

The term "pharmaceutically acceptable" as used herein means approved by a regulatory agency of the Federal or a state government, or listed in the U.S. Pharmacopeia, European Pharmacopeia or other generally recognized pharmacopeia An "analogue" of a chemical structure, as the term is used herein, refers to a chemical structure that preserves substantial similarity with the parent structure, although it may not be readily derived synthetically from the parent structure. A related chemical structure that is readily derived synthetically from a parent chemical structure is referred to as a "derivative."

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to an individual where the substance is converted in vivo by the action of biochemicals within the patient's body, such as enzymes, to the active pharmaceutical ingredient. Examples of prodrugs include esters of carboxylic acid groups, which can be hydrolyzed by endogenous esterases as are found in the bloodstream of humans and other mammals. Conventional procedures for the selection and preparation of suitable prodrug derivatives are described, for example, in "Design of Prodrugs", ed. H. Bundgaard, Elsevier, 1985.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH4+ or the cations of various amines, including tetraalkyl ammonium salts such as tetramethylammonium, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionisable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications.

Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of Formula (I) compounds, for example in their purification by recrystallization. All of these salts may be prepared by conventional means from the corresponding compound according to Formula (I) by reacting, for example, the appropriate acid or base with the compound according to Formula (I). The term "pharmaceutically acceptable salts" refers to nontoxic inorganic or organic acid and/or base addition salts, see, for example, Lit et al., Salt Selection for Basic Drugs (1986), Int J. Pharm., 33, 201-217, incorporated by reference herein.

The publications discussed herein are provided solely for their disclosure prior to the filing date of the present application. Nothing herein is to be construed as an admission that such publications constitute prior art to the claims appended hereto.

Pulmonary Endothelial Cell Dysfunction

Healthy pulmonary endothelial cells (PECs) are display a number of behaviours, including vascular tubule formation, vascular repair and anticoagulant properties. PEC dysfunction plays the major role in the development and progression of vascular pathology in PH, particularly PAH.

The term PEC dysfunction is well-known in the art (see, for example Humbert et al. European Respiratory Journal 2019, 53: 1801887; Ranchoux et al. Pulm. Circ. 2018, 8 (1):2045893217752912; Lai et al. J Physiol 2019, 597:1143-1156; and Franssen et al. ACC Heart Fail 2016, 4:312-324; each of which is incorporated herein by reference in its entirety). Accordingly as defined herein, the term "PEC dysfunction" typically encompasses any deviation from normal physiological PEC behaviours (also referred to interchangeably herein as phenotypes). PEC dysfunction may be defined as a deviation from normal physiological PEC, and typically include one or more abnormal phenotype. Non-limiting examples of such phenotypes include (i) an increase in pro-inflammatory activation; (ii) an increase in PEC apoptosis; (iii) an increase in reactive oxygen species (ROS) production; (iv) alteration (particularly an increase in) in vascular tone, which is typically associated with altered production of various endothelial vasoactive mediators, including NO, prostacyclin, endothelin-1 (ET-1), serotonin, and thromboxane (particularly, reduced production of NO and prostacyclin, and increased production of ET-1, serotonin and thromboxane); (v) active metabolic changes; (vi) a reduction in anticoagulant properties (for example a reduction in anticoagulant properties may associated with a decrease in P-selectin and/or Von Willebrand Factor (VWF) levels and/or an increase in the level of thrombomodulin); (vii) a reduction in vascular tubule formation; (viii) a reduction in vascular repair; (ix) disordered endothelial cell proliferation along with concurrent neoangiogenesis, particularly endothelia damage with hypoxia-induced proliferation; (x) a decrease in mitochondrial membrane potential and/or (xi) increased expression of markers of endothelial to mesenchymal transition; or any combination of (i) to (xi). PEC phenotypes which deviate from normal physiological PEC phenotypes are referred to herein as phenotypes of PEC dysfunction (also interchangeably referred to as PEC dysfunctional phenotypes).

PEC dysfunction may comprise pro-inflammatory activation of PECs. In other words, PEC dysfunction may be associated with an increase in PECs exhibiting a pro-inflammatory phenotype. A pro-inflammatory phenotype is typically associated with increased expression pro-inflammatory markers. Non-limiting examples of pro-inflammatory markers are E-selectin, ICAM1 and VCAM1. A pro-inflammatory phenotype is typically associated with increased release of inflammatory mediators, including certain cytokines and chemokines, including but not limited to IFN-gamma; IL1, 2, 6, 8, 10, 17, 18 or 21; IP10 (CXCL10); I-TAC (CXCL11); G-CSF; MCP-1; PAI1, TNF-alpha, RANTES, SDF-1 (CXCL12), or any combination thereof. Pro-inflammatory markers may be expression on the surface of PECs, or may be released from these cells, resulting in an increase in the circulating levels of these markers, particularly E-selectin and ICAM-1. Expression of these pro-inflammatory markers regulates inflammatory and immune cell recruitment and infiltration in PH lungs. PEC dysfunction may be associated with both an increase in the expression of pro-inflammatory markers and an increase in the expression and/or release of inflammatory mediators by PECs.

PEC dysfunction may comprise a deviation (i.e. an increase or decrease as appropriate) in any PEC phenotype, such as those described herein, of at least 5%, at least 10%, at least 20%, at least 30%, at least 40%, at least 50%, at least 60%, at least 70%, at least 80%, at least 90% or more. In the case of PEC dysfunction comprising a reducing in a PEC phenotype, this may include up to and including complete ablation of the phenotype. By way of non-limiting example, PEC dysfunction may comprise a reduction in vascular tubule formation of at least 30%, at least 40%, at least 50% or more.

Standard techniques and assays for quantifying PEC behaviours are known in the art and the selection of an appropriate assays would be routine for one of skill in the art. By way of non-limiting example, vascular tubule formation may be assays using a Matrigel tube formation assay, metabolic changes may be quantified using a glucose uptake assay, and/or PEC proliferation may be quantified using a cell proliferation assay. Exemplary techniques are used in the Examples below.

The invention relates to the use of agents which modulate translocator binding protein (TSPO) for inhibiting (referred to interchangeable herein as reducing) PEC dysfunction. Typically said TSPO modulating agents increase phenotypes associated with healthy PEC and/or inhibit phenotypes associated with PEC dysfunction as described herein, preferably both. Preferably the TSPO modulating agents of the invention are TSPO binding members as described herein.

Where PEC dysfunction involves an increase in a particular PEC phenotype, a TSPO modulating agent (e.g. a TSPO binding member) of the invention may reduce said phenotype (i.e. result in an absolute or relative reduction in said phenotype), or it may attenuate the increase in said phenotype (i.e. an individual may still exhibit an increase in the phenotype compared with said phenotype in a healthy control, but there is a reduction in the phenotype compared with the phenotype in said individual prior to treatment with the TSPO modulating agent). Reduction or inhibition of said phenotype is preferred.

Where PEC dysfunction involves an decrease in a particular PEC phenotype, a TSPO modulating agent (e.g. a TSPO binding member) of the invention may increase said phenotype (i.e. result in an absolute or relative increase in said phenotype), or it may attenuate the decrease in said phenotype (i.e. an individual may still exhibit an decrease in the phenotype compared with said phenotype in a healthy control, but there is an increase in the phenotype compared with the phenotype in said individual prior to treatment with the TSPO binding member). An increase of said phenotype is preferred.

By way of non-limiting example, a TSPO modulating agent (e.g. a TSPO binding member) of the invention may (i) reduce or attenuate an increase in pro-inflammatory activation; (ii) reduce or attenuate an increase in pulmonary endothelial cell apoptosis; (iii) reduce or attenuate an increase in reactive oxygen species (ROS) production; (iv) reduce or attenuate an increase in vascular tone (e.g. by modulating the expression of various endothelial vasoactive mediators, including NO, prostacyclin, endothelin-1 (ET-1), serotonin, and thromboxane); (v) reverse the active metabolic changes seen in pulmonary endothelial cell dysfunction (e.g. reverse the shift of mitochondrial glucose oxidation to cytoplasmic glycolysis, thus the increased cellular glucose uptake in the pulmonary vascular tissues; (vi) increase or attenuate a decrease in anticoagulant properties (for example, treatment may increase the level of P-selectin and/or Von Willebrand Factor (VWF), and/or may decrease the level of thrombomodulin, as described herein); (vii) increase or attenuate a decrease in vascular tubule formation; (viii) increase or attenuate a decrease in vascular repair; (ix) reduce or attenuate an increase in disordered endothelial cell proliferation and associated neoangiogenesis; (x) increase or attenuate a decrease in mitochondrial membrane potential; and/or (xi) reduce or attenuate an increase in expression of markers of endothelial to mesenchymal transition; or any combination of (i) to (xi).

A TSPO modulating agent (e.g. a TSPO binding member) of the invention may inhibit (protect against) pro-inflammatory activation of PECs, or attenuate an increase in the pro-inflammatory activation of PECs. In other words, a TSPO modulating agent (e.g. a TSPO binding member) of the invention may inhibit PECs from exhibiting a pro-inflammatory phenotype, such as the pro-inflammatory phenotypes as described herein. By way of non-limiting example, a TSPO modulating agent (e.g. a TSPO binding member) of the invention may inhibit expression of pro-inflammatory markers by PECs, particularly E-selectin, ICAM1 and/or VCAM1 (or attenuate an increase in the expression of such markers). A TSPO modulating agent (e.g. a TSPO binding member) of the invention may inhibit expression and/or release of inflammatory mediators, including certain cytokines and chemokines, including but not limited to IFN-gamma; IL1, 2, 6, 8, 10, 17, 18 or 21; IP10 (CXCL10); I-TAC (CXCL11); G-CSF; MCP-1; PAI1 TNF-alpha, RANTES, SDF-1 (CXCL12) (or attenuate an increase in the expression and/or release of such mediators). A TSPO modulating agent (e.g. a TSPO binding member) of the invention may inhibit expression of inflammatory markers on the surface of PECs, particularly E-selectin and/or ICAM-1. A TSPO modulating agent (e.g. a TSPO binding member) of the invention may inhibit (or attenuate an increase in) both expression of pro-inflammatory markers and expression and/or release of inflammatory mediators. Standard assays are known in the art for the detection and quantification of pro-inflammatory markers, with commercial products (e.g. Human Cytokine Antibody Array Panel A from R&D Systems) being readily available. A TSPO modulating agent of the invention may independently decrease the level of any one or more inflammatory mediator, e.g. any cytokine, chemokine or cell surface marker as described herein, by at least 1.5-fold, at least 2-fold, at least 3-fold, at least 4-fold, at least 5-fold or more compared with a suitable control (e.g. a corresponding patient or sample not treated with said TSPO modulating agent). Alternatively or in addition, a TSPO modulating agent of the invention may independently restore the level of any one or more inflammatory mediator, e.g. any cytokine, chemokine or cell surface marker as described herein, to within at least 5-fold, at least 4-fold, at least 3-fold, at least 2-fold, at least 1.5-fold, preferably to approximately baseline levels compared with a suitable control (e.g. a healthy control or individual not suffering from PEC dysfunction or an associated disease, such as PAH, as described herein).

A TSPO modulating agent (e.g. a TSPO binding member) of the invention may reduce or attenuate an increase in ROS production by at least 1.5-fold, at least 2-fold, at least 3-fold or more compared with a suitable control (e.g. a corresponding patient or sample not treated with said TSPO modulating agent). A TSPO modulating agent of the invention may independently restore the level of ROS production, to within at least 2-fold, at least 1.5-fold, preferably to approximately baseline levels compared with a suitable control (e.g. a healthy control or individual not suffering from PEC dysfunction or an associated disease, such as PAH, as described herein).

A TSPO modulating agent (e.g. a TSPO binding member) of the invention may increase or attenuate a decrease in mitochondrial membrane potential by at least 50%, at least 70%, at least 80%, at least 90%, at least 100%, at least 110%, at least 120%, at least 150% or more compared with a suitable control (e.g. a corresponding patient or sample not treated with said TSPO modulating agent). A TSPO modulating agent of the invention may independently restore the mitochondrial membrane potential, to within at least 2-fold, at least 1.5-fold, preferably to approximately baseline levels compared with a suitable control (e.g. a healthy control or individual not suffering from PEC dysfunction or an associated disease, such as PAH, as described herein).

A TSPO modulating agent (e.g. a TSPO binding member) of the invention typically does not have phosophodiesterase 1 (PDE) inhibitory activity, or does not inhibit PEC dysfunction by inhibition of PDE1. Thus, a TSPO modulating agent (e.g. a TSPO binding member) of the invention typically has a distinct mechanism of action compared with a PDE1 inhibitor.

In contrast to conventional treatments for PAH, TSPO modulators of the invention may not act to relax vascular tone and particularly may not act directly to relax vascular tone. Rather, TSPO modulators of the invention act to treat the underlying PEC dysfunction, as described herein, such as by reducing or attenuating an increase in vascular tone.

The effect of a TSPO modulating agent (e.g. a TSPO binding member) on a particular PEC phenotype may be compared with a suitable control, such as the same phenotype in the PEC from a healthy individual, or the phenotype in PEC from an individual (typically the same individual) with PEC dysfunction prior to treatment with the TSPO modulating agent (e.g. a TSPO binding member). When the control is the same phenotype an individual (typically the same individual) with PEC dysfunction prior to treatment with the TSPO modulating agent (e.g. a TSPO binding member), treatment with the TSPO modulating agent (e.g. a TSPO binding member) of the invention results in divergence of the phenotype from the dysfunctional baseline.

When the control is the same phenotype in the PEC from a healthy individual, treatment with a TSPO modulating agent (e.g. a TSPO binding member) of the invention results in a return of the phenotype towards the baseline of the healthy phenotype. In other words, the TSPO modulating agents (e.g. a TSPO binding member) of the invention restore normal healthy PEC phenotypes. This restoration may be partial, such as at least a 10%, at least a 20%, at least a 30%, at least a 40%, at least a 50%, at least a 60%, at least a 70%, at least an 80%, at least a 85%, at least a 90%, at least a 95%, at least a 96%, at least a 97%, at least a 98%, at least a 99% or more restoration of a normal PEC phenotype, up to and including a complete restoration of the normal PEC phenotype, such as any normal PEC phenotype as described herein.

By way of non-limiting example, treatment with a TSPO modulating agent of the invention (e.g. a TSPO binding member) may reduce (or attenuate an increase in) proliferation, particularly hypoxia-induced proliferation, of PECs. In particular, "treatment" may be defined as reducing the number of pulmonary PECs by at least 20%, at least 25%, at least 30%, at least 40%, at least 50% or more. Preferably, there is a reduction in the number of PECs of at least 30%, more preferably at least 40%. By way of further non-limiting example, treatment may reduce (or attenuate an increase in) apoptosis of PECs. In particular, "treatment" may be defined as reducing the number of apoptotic PECs by at least 20%, at least 25%, at least 30%, at least 40%, at least 50% or more. Preferably, there is a reduction in the number of apoptotic PECs of at least 30%, more preferably at least 40%.

The increase or decrease in any treatment outcome, including those listed above is typically assessed or quantified relative to the same phenotype or parameter in the disease state (e.g. in the same individual prior to treatment or in an individual with the same disease who has not been treated according to the invention. Thus, an appropriate control for assessing the increase or decrease in any treatment may be obtained from the same individual prior to treatment, or from a different individual with (clinically relevant) pulmonary endothelial cell dysfunction, particularly PH or PAH, but wherein the different individual has not been treated with a binding member of the invention, as described herein.

The terms "inhibit PEC dysfunction", "inhibition of PEC dysfunction" and "PEC dysfunction inhibitor" as used herein relate to inhibition of one or more phenotype of PEC dysfunction, and can be used interchangeably with the terms "reduce PEC dysfunction" and "reduction of PEC dysfunction".

As TSPO modulating agents (e.g. TSPO binding members) of the invention can inhibit PEC dysfunction, they can be used therapeutically in the treatment and/or prevention of PEC dysfunction. TSPO modulating agents (e.g. TSPO binding members) can also be used to treat and/or prevent diseases, disorders or conditions which are associated with PEC dysfunction, examples of which are described herein.

Accordingly, the present invention provides TSPO modulating agents (e.g. TSPO binding members) for use in the treatment and/or prevention of PEC dysfunction. The present invention also provides TSPO modulating agents (e.g. TSPO binding members) for use in the treatment and/or prevention of diseases or disorders associated with PEC dysfunction. Such TSPO modulating agent (particularly TSPO binding members) and associated vectors, compositions and drug delivery systems are described herein.

The invention relates to both direct and indirect modulation of TSPO. The term "modulation of TSPO" encompasses both up- and down-regulation of (i.e. increasing and decreasing as defined herein) both TSPO activity and/or expression. Typically the invention relates to modulation of TSPO activity. Unless explicitly stated, references herein to modulation of TSPO encompass both direct and indirect modulation of TSPO. Preferably, the invention relates to direct modulation of TSPO, wherein a TSPO binding member binds to TSPO and directly modulates its activity. Agents which modulate TSPO (either directly or indirectly) are referred to herein as "TSPO modulators".

"Direct modulation of TSPO" as used herein means modulation of the activity and/or expression of TSPO, i.e. without any intermediary step. By way of non-limiting example, direct inhibition of TSPO may elicited by competitive or non-competitive inhibitors of TSPO or by inhibition of a gene encoding TSPO. Direct up-regulation may be achieved, for example, by expression of a nucleic acid sequence encoding for TSPO. Preferably, direct modulation of TSPO activity is achieved using a TSPO binding member of the invention.

"Indirect modulation of TSPO" as used herein means modulation of the activity and/or expression of TSPO indirectly, i.e. through the modulation or delivery of genes/enzymes up- or down-stream of TSPO and/or through the generation or delivery of intermediaries which directly modulate TSPO. Indirect modulation may be elicited by upregulating the expression of an enzyme which generates an endogenous direct modulator of TSPO.

Expression may be quantified in terms of gene and/or protein expression, and may be compared with the expression of a control (e.g. housekeeping gene or protein). As a non-limiting example, in the context of TSPO expression, the actual amount of an TSPO gene, mRNA transcript and/or protein, such as the mass, molar amount, concentration or molarity of an TSPO gene, mRNA transcript and/or protein, or the number of mRNA molecules per cell in a sample obtained from an individual treated according to the invention and the control may be assessed, and compared with the corresponding value from the control. Alternatively, the expression of an TSPO gene and/or protein in a sample obtained from an individual treated according to the invention may be compared with that of the control without quantifying the mass, molar amount, concentration or molarity of the one or more gene and/or protein.

Typically, the control is an equivalent sample in which no modulation of TSPO expression has been effected. As a non-limiting example, in the case where an individual is treated with an agent that modulates expression, a suitable control would be a different individual to which the compound has not been administered or the same individual prior to administration of the compound. Conventional methods for the assessment of gene and/or protein expression are well known in the art and include RT-qPCR, ELISA, DNA microarray, RNA Seq, serial analysis of gene expression (SAGE) and western blotting.

In the context of the present invention, when referring to (direct or indirect) modulation of TSPO activity and/or expression, the degree of modulation may be as defined above.

Agents which Inhibit Pulmonary Endothelial Cell Dysfunction

The invention relates to the use of agents which modulate TSPO for the inhibition, and hence treatment and/or prevention of PEC dysfunction. In particular, the invention relates to the use of TSPO binding members for the inhibition, and hence treatment and/or prevention of PEC dysfunction and associated diseases and disorders.

Translocator protein (TSPO) is an 18 kDa conserved mitochondrial outer membrane protein, formerly known as the peripheral benzodiazepine receptor (PBR). Non-limiting exemplary human TSPO amino acid and nucleic acid sequences are provided herein. TSPO is highly expressed in inflammatory and endothelial cells. TSPO is widely distributed in tissues such as lung, heart, kidney, blood, gonads and adipocytes and associated with a wide range of biological processes including cell proliferation, apoptosis, steroidogenesis, and immunomodulation.

A modulator of TSPO according to the invention may selectively modulate TSPO (also referred to interchangeably herein as specifically modulating TSPO). This is typically the case for agents which directly modulate TSPO, particularly for TSPO binding members according to the invention. For such agents and particularly for TSPO binding members, selectivity may mean that the agent binds selectively (also referred to interchangeably herein as specifically) with TSPO. By "binds selectively", it will be understood that said agent (particularly a TSPO binding member) binds to TSPO, with no significant cross-reactivity to any other molecule. Cross-reactivity may be assessed by any suitable method. By way of non-limiting example, cross-reactivity of an agent which modulates TSPO (particularly a TSPO binding member) with a molecule other than TSPO may be considered significant if the agent binds to the other molecule at least 5%, 10%, 15%, 20%, 25%, 30%, 35%, 40%, 45%, 50%, 55%, 60%, 65%, 70%, 75%, 80%, 85%, 90% or 100% as strongly as it binds to TSPO. An agent that directly modulates TSPO (particularly a TSPO binding member) and that binds selectively to TSPO may bind to another molecule at less than 90%, 85%, 80%, 75%, 70%, 65%, 60%, 55%, 50%, 45%, 40%, 35%, 30%, 25% or 20% the strength that it binds to TSPO. Preferably, the agent that directly modulates TSPO (particularly a TSPO binding member) binds to the other molecule at less than 20%, less than 15%, less than 10% or less than 5%, less than 2% or less than 1% the strength that it binds to TSPO. By way of non-limiting example, a TSPO modulator of the invention may have no significant cross-reactivity with a phosphodiesterase (PDE), sodium channel and/or calcium channel.

A TSPO modulator of the invention may bind to TSPO with a Kd in the range of from about 1 nM to about 500 nM, such as from about 1 nM to about 250 nm, from about 1 nM to about 200 nM, from about 2 nM to about 100 nM, from about 2 nM to about 50 nM, from about 2 nM to about 40 nM, from about 2 nM to about 30 nM, from about 2.5 nM to about 20 nM, or from about 2.5 nM to about 10 nM.

A TSPO modulator of the invention may have a lower Kd value for so-called high affinity binders (human subjects who exhibit high-affinity binding of their TSPO to XBD-173) than their Kd value for so-called low affinity binders (human subjects who exhibit low-affinity binding of their TSPO to XBD-173). High affinity binders express two copies of the common allele at the rs6971 polymorphism (alanine at amino acid residue 147). Low affinity binders express two copies of the rare allele at the rs6971 polymorphism (A147T). By way of non-limiting example, a TSPO modulator of the invention may have a Kd for high affinity binders in the range of from about 1 nM to about 200 nM, such as from about 2 nM to about 100 nM, from about 2 nM to about 50 nM, from about 2 nM to about 40 nM, from about 2 nM to about 30 nM, from about 2.5 nM to about 20 nM. By way of further non-limiting example, alternatively or in addition, a TSPO modulator of the invention may have a Kd for low affinity binders in the range of from about 20 nM to about 50 μM, such as from about 200 nM to about 50 μM, from about 20 nM to about 500 nM, from about 30 nM to about 30 nM, from about 40 nM to about 500 nM, from about 30 nM to about 200M, or from about 30 nM to about 90 nM.

Any suitable agent which modulates TSPO may be used according to the present invention. Preferably TSPO binding members are used. Non-limiting examples of suitable TSPO modulating agents include small molecules, antibodies and antigen-binding fragments thereof, peptides and peptidomimetics, nucleic acids and aptamers, as described herein.

Typically agents which directly modulate TSPO are used. Preferably said agents are TSPO binding members. An agent which directly modulates TSPO, particularly a TSPO binding member, may be selected from a small molecule, a nucleic acid (for example, an siRNA, shRNA, or antisense oligonucleotide), antibody or antigen-binding fragment, or an aptamer. Preferably an agent which directly modulates TSPO is a binding member and/or a small molecule, even more preferably both.

An agent which indirectly modulates TSPO may be selected from a small molecule, a nucleic acid (for example, an siRNA, shRNA, or antisense oligonucleotide), antibody or antigen-binding fragment, or an aptamer.

An TSPO modulating agent of the invention, preferably a TSPO binding member, may be part of (comprised within) a pharmaceutical composition, preferably together with at least one pharmaceutically acceptable carrier. Examples of suitable pharmaceutical compositions (e.g. formulations) are described herein. The terms "pharmaceutically acceptable carrier" may be used interchangeably with the term "excipient" or "diluent" herein.

A combination of agents may be used to modulate TSPO. By way of non-limiting examples, a combination of agents may comprise: a direct modulator of TSPO (e.g. a TSPO binding member) and an indirect modulator of TSPO; at least two direct modulators of TSPO (e.g. two TSPO binding members or a TSPO binding member and another direct modulator of TSPO); or at least two indirect modulators of TSPO.

Small Molecules

Small molecules may be used as agents which modulate TSPO as described herein. In some embodiments, small molecule agents which are TSPO binding agents are preferred.

As defined herein, small molecules are low molecular weight compounds, typically organic compounds. Typically, a small molecule has a maximum molecular weight of 900 Da, and/or a molecular weight in the range of 200-800 Da, allowing for rapid diffusion across cell membranes. In some embodiments, the maximum molecular weight of a small molecule is 500 Da. Typically, a small molecule has a size in the order of 1 nm.

Standard techniques are known in the art for the production of small molecules, which can then readily be tested for the ability to bind to and/or modulate TSPO as described herein.

Examples of small molecule agents which are TSPO binding members and modulate TSPO include XBD-173 (described in more detail herein), ONO-2952, PK11195, PBR28, DPA713, DPA714, Ro 5-4864 FGIN-1-27, diazepam, lorazepam, midazolam, vinpocetine and etifoxine.

In some embodiments, the small molecule TSPO modulator is not vinpocetine, or is a small molecule TSPO binding member that is not vinpocetine. Thus, the small molecule TSPO modulator may be a TSPO binding member selected from XBD-173, ONO-2952, PK11195, PBR28, DPA713, DPA714, Ro 5-4864, FGIN-1-27, diazepam, lorazepam, midazolam, etifoxine, or a derivative or analogue thereof, optionally in the form of a pharmaceutically acceptable salt.

It will be understood that when small molecule TSPO modulating agents (e.g. TSPO binding members) of the present invention contain one or more chiral centres, the compounds may exist in, and may be isolated as pure enantiomeric or diastereomeric forms or as racemic mixtures. The present invention therefore includes any possible enantiomers, diastereomers, racemates or mixtures thereof of small molecule TSPO modulating agents (e.g. TSPO binding members) of the invention.

Small molecule TSPO modulating agents (e.g. TSPO binding members) of the present invention may have rotameric forms, or may not have rotational activity. Rotameric forms include slow rotating forms and fast rotating forms. In some preferred embodiments, fast rotating forms of the small molecule TSPO modulation agents (e.g. TSPO binding members) of the present invention are preferred.

A small molecule TSPO modulating agent (e.g. TSPO binding members) or a salt thereof may exhibit the phenomenon of tautomerism whereby two chemical compounds that are capable of facile interconversion by exchanging a hydrogen atom between two atoms, to either of which it forms a covalent bond. Since the tautomeric compounds exist in mobile equilibrium with each other they may be regarded as different isomeric forms of the same compound. The invention encompasses any tautomeric form of a small molecule TSPO modulating agent (e.g. TSPO binding member), and is not to be limited merely to any one tautomeric form. Thus, small molecule TSOP modulating agents (e.g. TSPO binding members) according to the invention encompass tautomers (including keto-enol and amide-imidic acid forms).

Small molecule TSPO modulating agents (e.g. TSPO binding members) may be used in the form of pro-drugs which convert into active small molecule TSPO modulating agents (e.g. TSPO binding members) in the body, analogues or derivates, as well as in salt, hydrate and solvate forms, as defined in the Definitions section herein.

XBD-173

The term "XBD-173" as used herein refers to N-Ethyl-7,8-dihydro-7-methyl-8-oxo-2-phenyl-N-(phenylmethyl)-9H-purine-9-acetamide, as well as derivatives or analogues thereof. Various synonyms of XBD-173 are known to the skilled person, including emapunil, AC-5216 and NVP-XBD173. XBD-173 has been assigned Chemical Abstracts Service registry number (CAS No.) 226954-04-7.

XBD-173 has the structure:

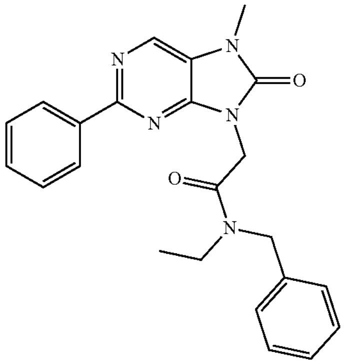 [SMILES: CCN(Cc1ccccc1)C(=O)Cn1c(=O)n(C)c2cnc(-c3ccccc3)nc21]

XBD-173 is a TSPO binding member that binds selectively to TSPO. There is some variation in the binding affinity for TSPO across human subjects. XBD-173 was originally developed as part of a drug discovery program for various CNS disorders, but CNS trials using XBD-173 were discontinued. Typically the Kd value of XBD-173 for human IPSO is in the range of from about 1 nM to about 50 nM, particularly from about 2 nM to about 35 nM. High affinity binders (human subjects who exhibit high-affinity binding of their TSPO to XBD-173) have a mean Kd of about 2.5 nM. Low affinity binders (human subjects who exhibit low-affinity binding of their TSPO to XBD-173) have a mean Kd of about 30 nM. Mixed affinity binders (human subjects who exhibit both high- and low-affinity binding sites on their TSPO for XBD-173) have a mean Kd of about 11 nM. These values were first investigated in Owen et al. Synapse (2011) 65 (3):257-259 (herein incorporated by reference in its entirety).

Typically, a derivative or analogue of XBD-173, or a pharmaceutically acceptable salt thereof is one that exhibits similar functional properties to XBD-173. Preferably, a derivative or analogue of XBD-173, or a pharmaceutically acceptable salt thereof is a TSPO binding member and modulates TSPO. A derivative or analogue of itaconate, or a pharmaceutically acceptable salt thereof, may exhibit improved TSPO binding and/or TSPO modulatory activity when compared to XBD-173, or may exhibit at least 50% (e.g. at least 60%, 70%, 80% or 90%) of the binding affinity of XBD-173 for TSPO, and/or at least 50% (e.g. at least 60%, 70%, 80% or 90%) of the TSPO modulatory activity of XBD-173.

References herein to XBD-173 include, derivatives, analogues, hydrates, solvates, prodrug and salt forms as described herein unless explicitly states to the contrary.

Aptamers

Aptamers are generally nucleic acid molecules that bind a specific target molecule. Aptamers can be engineered completely in vitro, are readily produced by chemical synthesis, possess desirable storage properties, and elicit little or no immunogenicity in therapeutic applications. These characteristics make them particularly useful in pharmaceutical and therapeutic utilities.

As used herein, "aptamer" refers in general to a single or double stranded oligonucleotide or a mixture of such oligonucleotides, wherein the oligonucleotide or mixture is capable of binding specifically to a target. Oligonucleotide aptamers will be discussed here, but the skilled reader will appreciate that other aptamers having equivalent binding characteristics can also be used, such as peptide aptamers.

In general, aptamers may comprise oligonucleotides that are at least 5, at least 10 or at least 15 nucleotides in length. Aptamers may comprise sequences that are up to 40, up to 60 or up to 100 or more nucleotides in length. For example, aptamers may be from 5 to 100 nucleotides, from 10 to nucleotides, or from 15 to 40 nucleotides in length. Where possible, aptamers of shorter length are preferred as these will often lead to less interference by other molecules or materials.

Aptamers may be generated using routine methods such as the Systematic Evolution of Ligands by Exponential enrichment (SELEX) procedure. SELEX is a method for the in vitro evolution of nucleic acid molecules with highly specific binding to target molecules. It is described in, for example, U.S. Pat. Nos. 5,654,151, 5,503,978, 5,567,588 and WO 96/38579.

The SELEX method involves the selection of nucleic acid aptamers and in particular single stranded nucleic acids capable of binding to a desired target, from a collection of oligonucleotides. A collection of single-stranded nucleic acids (e.g., DNA, RNA, or variants thereof) is contacted with a target, under conditions favourable for binding, those nucleic acids which are bound to targets in the mixture are separated from those which do not bind, the nucleic acid-target complexes are dissociated, those nucleic acids which had bound to the target are amplified to yield a collection or library which is enriched in nucleic acids having the desired binding activity, and then this series of steps is repeated as necessary to produce a library of nucleic acids (aptamers) having specific binding affinity for the relevant target.

Peptides and Peptidomimetics

In addition, the invention encompasses the use of peptide and peptidomimetic agents to modulate TSPO, and particularly as TSPO binding members of the invention. For example, the use of peptides, stapled peptides, peptoids and peptidomimetics that would directly or indirectly modulate TSPO is embraced by the present invention.

Peptidomimetics are compounds which mimic a natural peptide or protein with the ability to interact with the biological target and produce the same biological effect. Peptidomimetics may have advantages over peptides in terms of stability and bioavailability associated with a natural peptide. Peptidomimetics can have main- or side-chain modifications of the parent peptide designed for biological function. Examples of classes of peptidomimetics include, but are not limited to, peptoids and β-peptides, as well as peptides incorporating D-amino acids.

Methods for producing synthetic peptides and peptidomimetics (such as peptoids) are known in the art, as are the sequences of TSPO and its ligands. Thus, it would be routine for one of skill in the art to produce suitable synthetic peptides and peptidomimetics which directly or indirectly modulate TSPO using known techniques and based on the known TSPO and TSPO ligand sequences. Thus, it would be routine for one of skill in the art to generate peptide or peptidomimetic TSPO binding members for use in the present invention.

Antibodies and Antigen-Binding Fragments Thereof

An agent which modulates TSPO, particularly a TSPO binding member, may be an antibody, or an antigen binding fragment thereof as defined herein. An antibody according to the invention may be polyclonal or monoclonal, preferably monoclonal.

An antibody of the invention and antigen-binding fragments thereof may be derived from any species by recombinant means. For example, the antibodies or antigen-binding fragments may be mouse, rat, goat, horse, swine, bovine, chicken, rabbit, camelid, donkey, human, or chimeric versions thereof. For use in administration to humans, non-human derived antibodies or antigen-binding fragments may be genetically or structurally altered to be less antigenic upon administration to the human patient.

Human or humanized antibodies are preferred, especially as recombinant human or humanized antibodies as defined herein.

An antibody of the invention and antigen-binding fragments thereof disclosed herein can be further modified using conventional techniques known in the art, for example, by using amino acid deletion(s), insertion(s), substitution(s), addition(s), and/or recombination(s) and/or any other modification(s) known in the art, either alone or in combination. Methods for introducing such modifications in the DNA sequence underlying the amino acid sequence of an immunoglobulin chain arc well known to the person skilled in the art.

The antibodies of the invention or antigen-binding fragments thereof may have any antibody format. In some embodiments, the antibody has the "conventional" format described above. Alternatively, the antibody can be in some embodiments a Fab fragment. The antibody according to the invention can also be a Fab', an Fv, an scFv, an Fd, a V NAR domain, an IgNAR, an intrabody, an IgG CH2, a minibody, a single-domain antibody, an Fcab, an scFv-Fc, F(ab')2, a di-scFv, a bi-specific T-cell engager (BITE®), a F(ab')3, a tetrabody, a triabody, a diabody, a DVD-Ig, an (scFv)2, or a mAb2.

Nucleic Acids

The agents which modulate TSPO according to the invention may be nucleic acids as defined herein.

A nucleic acid agent of the invention may modulate TSPO expression. Such nucleic acids include "antisense nucleic acids", by which is meant an RNA or DNA molecule that binds to another RNA or DNA (target RNA, DNA), whether an TSPO RNA or DNA as defined herein (e.g. in the case of direct TSPO modulation), or a non-TSPO RNA or DNA (e.g. in the case of indirect modulation). Non-limiting examples of antisense nucleic acids include, for example, antisense RNA or DNA molecules, interference RNA (RNAi), micro RNA, decoy RNA molecules, siRNA, enzymatic RNA, therapeutic editing RNA and agonist and antagonist RNA, antisense oligomeric compounds, antisense oligonucleotides, external guide sequence (EGS) oligonucleotides, alternate splicers, primers, probes, and other oligomeric compounds that hybridize to at least a portion of the target nucleic acid (such as the TSPO gene). As such, these nucleic acids may be introduced in the form of single-stranded, double-stranded, partially single-stranded, or circular oligomeric compounds.

A nucleic acid agent of the invention may increase TSPO expression. By way of non-limiting example, a nucleic acid of the invention may comprise a nucleic acid sequence encoding for TSPO as defined herein. Typically, the nucleic acid sequence encoding for TSPO is operably linked to a promoter capable to expressing said nucleic acid sequence. Examples of inducible and non-inducible promoters are known in the art. Thus, it would be routine for one of skill in the art to select a suitable promoter.

A nucleic acid of the invention may increase TSPO expression through modulation of an upstream transcriptional program.

Vectors and Plasmids

The present invention provides a vector that expresses an TSPO modulating agent (e.g. a TSPO binding member) of the invention. In other words, a TSPO modulating agent (e.g. a TSPO binding member) of the invention may be provided by means of a vector.

The vector may be a viral vector. Such a viral vector may be an adenovirus (of a human serotype such as AdHu5, a simian serotype such as ChAd63, ChAdOXI or ChAdOX2, or another form), an adeno-associated viral (AAV) vector or poxvirus vector (such as a modified vaccinia Ankara (MVA)). ChAdOXI and ChAdOX2 are disclosed in WO2012/172277. ChAdOX2 is a BAC-derived and E4 modified AdC68-based viral vector.

Viral vectors are usually non-replicating or replication impaired vectors, which means that the viral vector cannot replicate to any significant extent in normal cells (e.g. normal human cells), as measured by conventional means—e.g. via measuring DNA synthesis and/or viral titre. Non-replicating or replication impaired vectors may have become so naturally (i.e. they have been isolated as such from nature) or artificially (e.g. by breeding in vitro or by genetic manipulation). There will generally be at least one cell-type in which the replication-impaired viral vector can be grown—for example, modified vaccinia Ankara (MVA) can be grown in CEF cells. In one embodiment, the vector is selected from a human or simian adenovirus, AAV or a poxvirus vector.

Typically, the viral vector is incapable of causing a significant infection in an animal individual, typically in a mammalian individual such as a human or other primate.

The invention further provides a DNA vector that expresses a TSPO modulating agent (e.g. a TSPO binding member) of the invention, such as a plasmid-based DNA vaccine. In one embodiment the DNA vector is capable of expression in a mammalian cell expression system, such as an immunised cell.

The vector may be an RNA vector, such as a self-amplifying RNA vaccine (Geall, A. J. et al., Proc Natl Acad Sci USA 2012; 109 (36) pp. 14604-9, herein incorporated by reference).

The present invention also provides virus-like particles (VLP) and/or fusion proteins comprising a TSPO modulating agent (e.g. a TSPO binding member) of the invention, as described herein. References herein to vectors of the invention may apply equally to VLP and/or fusion proteins of the invention.

Drug Delivery Systems

An agent, vector or composition of the invention may be delivered by means of a drug delivery system. Drug delivery systems may be used to increase delivery of an agent, vector or composition of the invention; increase uptake of an agent, vector or composition of the invention by a target cell or tissue; and/or to increase the efficacy of an agent, vector or composition of the invention.

Any appropriate drug delivery system may be used to deliver an agent, vector or composition of the invention. Conventional drug delivery systems are known in the art. By way of non-limiting example, appropriate drug delivery systems include liposomes, immunoliposomes, nanoparticles and conjugates. Thus, it would be routine for one of skill in the art to select a suitable drug delivery system. Liposome drug delivery systems are referred to interchangeably herein as liposome-based drug delivery systems.

The skilled person would understand that the choice of drug delivery system may depend on the particular indication and/or tissue to be treated.

As discussed herein, the present invention relates to the inhibition and treatment and/or prevention of PEC dysfunction. Therefore, drug delivery systems (e.g. liposomes or nanoparticles) specifically adapted for endothelial cells, particularly PECs, may be used according to the invention. For example, drug delivery systems which specifically or preferentially target endothelial cells may be used according to the invention. Such liposome drug delivery systems may further be conjugated to antibodies, or antigen binding fragments thereof, which target endothelial cell (particularly PEC)-specific cell surface markers. Exemplary markers, such as E-selectin, ICAM1 and VCAM1 are described herein. Typically, the drug delivery systems will have an average size of between 1 to 5 μm, preferably 1.5 to 2 μm.

Therapeutic Indications

The TSPO modulating agents (particularly TSPO binding members), vectors, compositions and drug delivery systems as described herein are useful in the treatment of PEC dysfunction. PEC is described herein.

PEC dysfunction plays a major role in the development and progression of vascular pathology in pulmonary hypertension (PH), including pulmonary arterial hypertension (PAH) and other related diseases and disorders. Without being bound by theory, PEC dysfunction typically involves pro-inflammatory activation of PECs. This typically results in the expression of pro-inflammatory markers and the release of pro-inflammatory mediators into the pulmonary vasculature (as described herein). These pro-inflammatory markers include adhesion molecules such as E-selectin, ICAM1 and VCAM1. Surface expression of such markers and adhesion molecules, together with release of pro-inflammatory mediators drive inflammatory and immune cell recruitment and infiltration into the lung, which can drive pathological restructuring of the pulmonary vasculature. This restructuring can affect PECs as well as smooth muscle cells and fibroblasts within the pulmonary vasculature, typically by stimulating proliferation of these cells. Inflammation and excessive proliferation of these vascular cells leads to increased pulmonary vascular resistance and chronic elevation of pulmonary arterial pressure (PAP), which can ultimately result in hypertrophy of the right heart and eventually heart failure.

Although differing in aetiology and causative mechanisms, different types of PH and associated heart failures are all associated with PEC dysfunction. Due to this common mechanism the TSPO modulating agents (particularly TSPO binding members), compositions and drug delivery systems of the invention are useful in treating any disease or disorder associated with PEC dysfunction, including PH and associated heart failures.

Accordingly, the present invention relates to the treatment and/or prevention of PH and/or heart failure. The invention particularly relates to the treatment and/or prevention of PAH (including idiopathic PAH (IPAH)) and/or heart failure with preserved ejection fraction and associated pulmonary hypertension (PH-HFpEF). Preferably the invention relates to the treatment of PAH and/or HFpEF.

Treatment Outcomes

"Treatment" according to the present invention may be defined as providing a treatment outcome as defined below. These definitions may apply to therapeutic and prophylactic treatments as described herein.

As described herein, the invention relates to the use of agents which modulate TSPO (such as TSPO binding members) for inhibiting PEC dysfunction. Typically said TSPO modulating agents increase phenotypes associated with healthy PEC and/or inhibit phenotypes associated with PEC dysfunction as described herein, preferably both.

Accordingly, a treatment outcome according to the present invention may be inhibition of one or more phenotype associated with PEC dysfunction and/or an increase in one or more phenotype associated with healthy PEC, as described herein. Examples of such treatment outcomes associated with PECs are described herein.

Treatment may reduce (or attenuate an increase in) proliferation, particularly hypoxia-induced proliferation, of PECs. In particular, "treatment" may be defined as reducing the number of PECs by at least 20%, at least 25%, at least 30%, at least 40%, at least 50% or more. Preferably, there is a reduction in the number of PECs of at least 30%, more preferably at least 40%.

Treatment may reduce (or attenuate an increase in) apoptosis of PECs. In particular, "treatment" may be defined as reducing the number of apoptotic PECs by at least 20%, at least 25%, at least 30%, at least 40%, at least 50% or more. Preferably, there is a reduction in the number of apoptotic PECs of at least 30%, more preferably at least 40%. Standard apoptosis assays are known in the art.

Treatment may increase (or attenuate a decrease in) vascular tubule formation by PECs. In particular, "treatment" may be defined as increasing vascular tubule formation by at least 20%, at least 25%, at least 30%, at least 40%, at least 50% or more. Preferably, there is an increase in vascular tubule formation of at least 30%, more preferably at least 40%. Suitable assays for measuring vascular tubule formation are known in the art and would be routine for one of skill in the art. For example, ex vivo angiogenesis assays (commonly carried out in Matrigel®), may be used to measure the length of tubule sprouts and/or fluorescent imaging may be used to identify tubules by staining the tissue with calcein (Invitrogen).

Treatment may increase (or attenuate a decrease in) vascular repair (e.g. by PECs). In particular, "treatment" may be defined as increasing vascular repair by at least 20%, at least 25%, at least 30%, at least 40%, at least 50% or more. Preferably, there is an increase in vascular repair of at least 30%, more preferably at least 40%.

Treatment may decrease pulmonary vascular resistance. In particular, "treatment" may be defined as decreasing pulmonary vascular resistance by at least 5%, at least 10%, at least 15%, at least 20%, at least 25%, at least 30% or more. Preferably, there is a decrease of at least 10% in pulmonary vascular resistance.

Treatment may increase (or attenuate a decrease in) the right ventricular ejection fraction. In particular, "treatment" may be defined as increasing the right ventricular ejection fraction by at least 5%, at least 10%, at least 15%, at least 20%, at least 25%, at least 30% or more. Preferably, there is an increase of at least 10% in the right ventricular ejection fraction.

Treatment may increase (or attenuate a decrease in) anticoagulant properties of PECs. In particular, "treatment" may be defined as increasing anticoagulant properties of PECs by at least 20%, at least 25%, at least 30%, at least 40%, at least 50% or more. Preferably, there is an increase in anticoagulant properties of PECs of at least 30%, more preferably at least 40%. Suitable assays are known in the art. For example, anticoagulant properties may be assessed by determining P-selectin and/or Von Willebrand Factor (VWF) levels (increased levels being associated with an increase in anticoagulant properties) and/or thrombomodulin (decreased levels being associated with an increase in anticoagulant properties), Thus, "treatment" may be defined as increasing P-selectin and/or VWF levels by at least 20%, at least 25%, at least 30%, at least 40%, at least 50% or more, preferably at least 30%, more preferably at least 40%. Alternatively or in addition, "treatment" may be defined as decreasing thrombomodulin levels by at least 20%, at least 25%, at least 30%, at least 40%, at least 50% or more, preferably at least 30%, more preferably at least 40%.

Treatment may be defined as reversing the active metabolic changes seen in PEC dysfunction. Active metabolic changes can be assessed by determining the level of glucose metabolism enzymes and glucose uptake. Suitable assays are known in the art, such as 2DG uptake assays and FDG tissue uptake assays (assessed using PET). Typically, treatment results in a decrease in 2DG and/or FDG uptake. More specifically, treatment may result in a decrease in right ventricular 2DG uptake and/or a decrease in FDG uptake by the myocardium.

Treatment may reduce (or attenuate an increase in) reactive oxygen species (ROS) production (e.g. by PECs). Suitable assays are known in the art and would be routine for the skilled person. Examples include ROS/superoxide detection (SOD) assays, wherein ROS/SOD can be monitored using fluorescence microscopy, flow cytometry or microplate readers. In particular, "treatment" may be defined as reducing ROS production by at least 20%, at least 25%, at least 30%, at least 40%, at least 50% or more. Preferably, there is a reduction in ROS production of at least 30%, more preferably at least 40%.

Treatment may reduce (or attenuate an increase in) pro-inflammatory activation of PECs. In particular, "treatment" may be defined as reducing pro-inflammatory activation of PECs by at least 20%, at least 25%, at least 30%, at least 40%, at least 50% or more. Preferably, there is a reduction in pro-inflammatory activation of PECs of at least 30%, more preferably at least 40%. Accordingly, treatment may reduce (or attenuate an increase in) expression of a pro-inflammatory phenotype by PECs, such as the pro-inflammatory phenotypes as described herein. In particular, "treatment" may be defined as reducing expression of a pro-inflammatory phenotype by PECs by at least 20%, at least 25%, at least 30%, at least 40%, at least 50% or more. Preferably, there is a reduction in expression of a pro-inflammatory phenotype by PECs of at least 30%, more preferably at least 40%. By way of non-limiting example, treatment may inhibit expression of pro-inflammatory markers by PECs, particularly E-selectin, ICAM1 and/or VCAM1 (or attenuate an increase in the expression of such markers). Other pro-inflammatory markers that may be decreased (or an increase in expression attenuated) according to the invention include cytokines, chemokines, and acute phase proteins, such as IFN-gamma; IL1, 2, 6, 8, 10, 17, 18, 21; IP10 (CXCL10); I-TAC (CXCL11); G-CSF; MCP-1; PAI1, TNF-alpha, RANTES and/or SDF-1 (CXCL12). Other conventional assays for quantifying pro-inflammatory activation are known in the art and may be used according to the invention. Treatment may inhibit expression and/or release of inflammatory mediators, including certain cytokines and chemokines (or attenuate an increase in the expression and/or release of such mediators), as described herein. Treatment may result in a reduction in the expression of pro-inflammatory markers and the expression and/or release of inflammatory mediators.

Treatment may reduce (or attenuate an increase in) expression of markers of endothelial to mesenchymal transition (EndMT) in PECs. In particular, "treatment" may be defined as reducing expression of markers of endothelial to mesenchymal transition in PECs by at least 20%, at least 25%, at least 30%, at least 40%, at least 50% or more. Preferably, there is a reduction in expression of markers of endothelial to mesenchymal transition in PECs of at least 30%, more preferably at least 40%. Non-limiting examples of such EndMT markers include α-SMA and collagen 1. Alternatively or in addition, treatment may increase (or attenuated a decrease in) expression of endothelial cell markers. Thus, "treatment" may be defined as increasing expression of endothelial cell markers in PECs by at least 20%, at least 25%, at least 30%, at least 40%, at least 50% or more preferably at least 30%, more preferably at least 40%. Non-limiting examples of such endothelial cell markers include CD31, VWF and/or VE-cadherin. Lung-specific endothelial cell markers include vimentin and twist 1.

Treatment may regulate vascular tone (e.g. by modulating the expression of various endothelial vasoactive mediators, including NO, prostacyclin, endothelin-1 (ET-1), serotonin, and thromboxane). In particular, "treatment" may be defined as decreasing vascular tone by at least 20%, at least 25%, at least 30%, at least 40%, at least 50% or more, preferably by at least 30%, more preferably at least 40%. Vascular tone may be quantified using standard assays known in the art, such as by determining pulmonary arterial pressure measured by right heart catheterization.

Treatment may increase (or attenuate a decrease in) the mitochondrial potential of PECs. In particular, "treatment" may be defined as increasing the mitochondrial potential of PECs by at least at least 50%, at least 70%, at least 80%, at least 90%, at least 100%, at least 110%, at least 120%, at least 150% or more. Preferably, there is an increase in the mitochondrial potential of PECs of at least 70%, more preferably at least 80% or more. Suitable assays are known in the art and described in the Examples herein. Alternatively or in addition, treatment may increase (or attenuate a decrease in) the mitochondrial potential of other cell types, such as pulmonary smooth muscle cells, or other cell types described herein.

Treatment according to the present invention may also have an effect on other cells of the pulmonary vasculature, and/or also on the structure and function of the heart. Accordingly, treatment outcomes of the present invention may additionally or alternatively encompass these other effects.

Treatment may reduce (or attenuate an increase in) proliferation, particularly hypoxia-induced proliferation, of pulmonary smooth muscle cells, particularly smooth muscle cells of the pulmonary vascular, such as pulmonary artery smooth muscle cells. In particular, "treatment" may be defined as reducing the number of pulmonary smooth muscle cells (pulmonary vascular smooth muscle cells) by at least 20%, at least 25%, at least 30%, at least 40%, at least 50% or more. Preferably, there is a reduction in the number of pulmonary smooth muscle cells (pulmonary vascular smooth muscle cells) of at least 30%, more preferably at least 40%. Suitable proliferation assays are routine in the art.

Treatment may reduce (or attenuate an increase in) proliferation, particularly hypoxia-induced proliferation, of pulmonary vasculature fibroblasts. In particular, "treatment" may be defined as reducing the number of pulmonary vasculature fibroblasts by at least 20%, at least 25%, at least 30%, at least 40%, at least 50% or more. Preferably, there is a reduction in the number of pulmonary vasculature fibroblasts of at least 30%, more preferably at least 40%. Suitable proliferation assays are routine in the art.

Treatment may reduce (or attenuate an increase in) apoptosis of pulmonary smooth muscle cells, particularly smooth muscle cells of the pulmonary vascular, such as pulmonary artery smooth muscle cells. In particular, "treatment" may be defined as reducing the number of apoptotic pulmonary smooth muscle cells (pulmonary vascular smooth muscle cells) by at least 20%, at least 25%, at least 30%, at least 40%, at least 50% or more. Preferably, there is a reduction in the number of apoptotic pulmonary smooth muscle cells (pulmonary vascular smooth muscle cells) of at least 30%, more preferably at least 40%. Suitable apoptosis assays are routine in the art.

Treatment may reduce (or attenuate an increase in) apoptosis of pulmonary vasculature fibroblasts. In particular, "treatment" may be defined as reducing the number of apoptotic pulmonary vasculature fibroblasts by at least 20%, at least 25%, at least 30%, at least 40%, at least 50% or more. Preferably, there is a reduction in the number of apoptotic pulmonary vasculature fibroblasts of at least 30%, more preferably at least 40%. Suitable apoptosis assays are routine in the art.

Treatment may reduce (or attenuate an increase in) pulmonary vasculature remodelling. In particular, "treatment" may be defined as reducing pulmonary vasculature remodelling by at least 20%, at least 25%, at least 30%, at least 40%, at least 50% or more. Preferably, there is a reduction in pulmonary vasculature remodelling of at least 30%, more preferably at least 40%. Pulmonary vascular remodelling may correspond with the percentage of smooth muscle cells within the pulmonary vasculature. Accordingly, "treatment" resulting in a reduction in pulmonary vasculature remodelling may be defined as reducing the number of pulmonary vasculature smooth muscle cells by at least 20%, at least 25%, at least 30%, at least 40%, at least 50% or more. Preferably, there is a reduction in the number of pulmonary vasculature smooth muscle cells of at least 30%, more preferably at least 40%. Other parameters are known in the art as metrics for pulmonary vascular remodelling, including peripheral vascular lumen occlusion and a shift towards mesenchymal transformation (can be detected by marker expression). Therefore one of skill in the art would readily be able to determine whether treatment results in a reduction (or attenuation of an increase in) pulmonary vasculature remodelling using any of these parameters.

Treatment may reduce (or attenuate an increase in) infiltration of inflammatory cells into the lungs. Non-limiting examples of such inflammatory cells include $CD68^+$ macrophages [. In particular, "treatment" may be defined as reducing the infiltration of inflammatory cells, such as $CD68^+$ macrophages, by at least 20%, at least 25%, at least 30%, at least 40%, at least 50% or more. Preferably, there is a reduction in infiltration of inflammatory cells, such as $CD68^+$ macrophages, of at least 30%, more preferably at least 40%.

Treatment may reduce (or attenuate an increase in) pulmonary arterial pressure (PAP). In particular, "treatment"

may be defined as resulting in a reduction in PAP by at least 20%, at least 25%, at least 30%, at least 40%, at least 50% or more. Preferably, there is a reduction in PAP of at least 30%, more preferably at least 40%.

Treatment may reduce (or attenuate an increase in) glucose uptake by cells of the lung, particularly cells of the pulmonary vasculature (such as PECs, smooth muscle cells and/or fibroblasts, preferably PECs), and/or inflammatory cells (particularly $CD68^+$ cells) that have infiltrated the pulmonary vasculature and the lungs. In particular, "treatment" may be defined as reducing glucose uptake by cells of the lung, preferably cells of the pulmonary vasculature (such as PECs, smooth muscle cells and/or fibroblasts) and/or inflammatory cells (particularly $CD68^+$ cells) that have infiltrated the pulmonary vasculature and the lungs by at least 20%, at least 25%, at least 30%, at least 40%, at least 50% or more. Preferably, there is a reduction in glucose uptake by cells of the lung, preferably cells of the pulmonary vasculature (such as PECs, smooth muscle cells and/or fibroblasts) and/or inflammatory cells (particularly $CD68^+$ cells) that have infiltrated the pulmonary vasculature and the lungs of at least 40%, more preferably at least 50%. Standard assays for determining glucose uptake are known in the art, with examples as described herein.

Treatment may reduce (or attenuate an increase in) right ventricular systolic pressure (RVSP). In particular, "treatment" may be defined as resulting in a reduction in RVSP by at least 20%, at least 25%, at least 30%, at least 40%, at least 50% or more. Preferably, there is a reduction in RVSP of at least 30%, more preferably at least 40%.

Treatment may reduce (or attenuate an increase in) right ventricular hypertrophy (RVH). RVH may be defined by an increase in the measurement of the ration of RV:LV+septum, or RV:body weight. In particular, "treatment" may be defined as resulting in a reduction in RVH of at least 20%, at least 25%, at least 30%, at least 40%, at least 50% or more. Preferably, there is a reduction in RVH of at least 30%, more preferably at least 40%. Preferably, the RVH is cardiomyocyte hypertrophy in the RV. Preferably, therefore, "treatment" may be defined as resulting in a reduction in cardiomyocyte hypertrophy in the RV of at least 20%, at least 25%, at least 30%, at least 40%, at least 50% or more. Preferably, there is a reduction in cardiomyocyte hypertrophy in the RV of at least 30%, more preferably at least 40%.

Treatment may reduce (or attenuate an increase in) glucose uptake by cells of the heart, particularly cardiomyocytes. Typically treatment reduces (or attenuates an increase in) cells of the RV, preferably cardiomyocytes of the RV. In particular, "treatment" may be defined as reducing glucose uptake by cells of the heart, particularly cardiomyocytes (preferably of the RV) by at least 20%, at least 25%, at least 30%, at least 40%, at least 50%, at least 60%, at least 70% or more. Preferably, there is a reduction in glucose uptake by cells of the lung, preferably cells of the pulmonary vasculature (such as PECs, smooth muscle cells and/or fibroblasts) of at least 40%, more preferably at least 50%.

Treatment may reduce (or attenuate an increase in) remodelling of the heart, particularly the RV. This may be defined by an increase in the measurement of the ration of RV:LV+septum, or RV:body weight. In particular, "treatment" may be defined as reducing remodelling of the heart, particularly the RV, by at least 20%, at least 25%, at least 30%, at least 40%, at least 50% or more. Preferably, there is a reduction in remodelling of the heart, particularly the RV, of at least 30%, more preferably at least 40%.

Treatment may increase (or attenuate a decrease in) capillary density within the cardiac tissue, particularly the RV. In particular, "treatment" may be defined as increasing capillary density within the cardiac tissue, particularly the RV, by at least 20%, at least 25%, at least 30%, at least 40%, at least 50% or more. Preferably, there is an increase in capillary density within the cardiac tissue, particularly the RV, of at least 30%, more preferably at least 40%. Suitable assays are known in the art, including immunofluorescence of cardiac tissue sections staining for the number of $CD31^+$ microvessels, and are routine for one of skill in the art.

Treatment may improve (or attenuate a decrease in) cardiac performance. In particular, "treatment" may be defined as improving cardiac performance by at least 20%, at least 25%, at least 30%, at least 40%, at least 50% or more. Preferably, there is an improvement of cardiac performance of at least 30%, more preferably at least 40%. Techniques for determining/quantifying cardiac output are known in the art. For example, a cardiac MRI may be used for anatomical, volumetric and functional evaluation. Specific metrics of cardiac performance (RVEDVI, RVEF, EES/Ea) that may be assessed by MRI are described below. These MRI indexes are translational: a decreased stroke volume, increased RV end-diastolic volume and decreased RVEF at MRI predict a poor outcome in patients with PAH Treatment may reduce (or attenuate an increase in) right ventricular (RV) end-diastolic volume index (RVEDVI). In particular, "treatment" may be defined as reducing RVEDVI by at least 20%, at least 25%, at least 30%, at least 40%, at least 50% or more. Preferably, there is a reduction in remodelling of the heart, particularly the RV, of at least 30%, more preferably at least 40%.

Treatment may improve (or attenuate a decrease in) RV ejection fraction (RVEF). In particular, "treatment" may be defined as improving RVEF by at least 20%, at least 25%, at least 30%, at least 40%, at least 50% or more. Preferably, there is an improvement of cardiac performance of at least 20%, more preferably at least 30%, even more preferably at least 40%.

Treatment may improve (or attenuate a decrease in) the ratio of chamber elastance (EEs): effective arterial elastance (Ea), which is a routine measure of heart (RV) and artery (pulmonary artery, PA) coordination/coupling. In particular, "treatment" may be defined as improving EEs:Ea by at least 20%, at least 25%, at least 30%, at least 40%, at least 50% or more. Preferably, there is an improvement of EEs:Ea of at least 20%, more preferably at least 30%, even more preferably at least 40%.

Treatment according to the present invention may result in any combination of the treatment outcomes as described herein. Typically treatment according to the invention results in a treatment outcome or combination of treatment outcomes that is associated with a reduction in clinical risk. Several clinical registries exist, each with a well-established formula or calculator to determine clinical risk, typically by calculation of a clinical risk score. Common registers include the French Pulmonary Hypertension Network (FPHN) registry risk equation, the PH connection equation, the Scottish composite score, the US Registry to Evaluate Early and Long-term PAH Disease Management (REVEAL) risk equation and risk score, and the 2015 ESC/ERS PH guidelines risk table. By way of non-limiting example, the REVEAL equation stratifies risk as follows: low risk=REVEAL score≤6, intermediate risk=REVEAL score 7 and 8, and high risk=REVEAL score≥9. The FPHN assessment includes assessment for four low-risk criteria: (i) World Health Organization (WHO)/New York Heart Association Functional Class (FC) I or II; (ii) 6-min walk distance (6MWD) >440 m; (iii) right atrial pressure (RAP) <8 mmHg; and (iv) cardiac index≥2.5 $Lmin^{-1}$ $m^{-2}$. Each of these registries and equations would be well-known to persons working in the field of pulmonary hypertension. These four registers and their clinical risk equations/scores are described in Galiè et al. (Eur. Respir. J. (2019) 53:1801889), which is herein incorporated by reference in its entirety, the section entitled "Risk stratification" being particularly relevant. Therefore, treatment according to the invention typically results in a treatment outcome or combination of treatment outcomes that is associated with a reduction in clinical risk as measured using any of the FPHN registry risk equation, the PH connection equation, the Scottish composite score, the REVEAL risk equation and risk score, and the 2015 ESC/ERS PH guidelines risk table. Other registries and equations that may be used include the Swedish PAH Register and the Prospective Registry of Newly Initiated Therapies for Pulmonary Hypertension (COMPERA) registry. Treatment according to the present invention typically results in a treatment outcome or combination of treatment outcomes that is associated with a reduction in clinical risk of at least one stratification level (e.g. from high risk to intermediate risk, or from intermediate risk to low risk), as assessed using a relevant clinical registry/equation.

Treatment according to the present invention may have no effect or minimal effect on systemic blood pressure. The term "no or minimal effect" encompasses less than a 10% change, less than a 5%, less than a 2% change down to no change in systemic blood pressure on treatment according to the invention.

For the avoidance of doubt, treatment according to the present invention typically does not result in an increase in cardiac hypertrophy, particularly RVH. Rather, as described herein, treatment may reduce (or attenuate an increase in) cardiac hypertrophy, particularly RVH.

A suitable control may be used as described herein. By way of non-limiting example, one or more treatment outcome in an individual treated according to the present invention may be compared with a suitable control, such as the same parameter in healthy individual, or the parameter in an individual (typically the same individual) with PEC dysfunction prior to treatment.

Therapy

The invention provides a TSPO modulating agent (as described herein, particularly TSPO binding members), vectors and compositions comprising said TSPO modulating agent (particularly TSPO binding members), drug delivery systems for delivering said agent for use in the treatment and/or prevention of PEC dysfunction and associated diseases and disorders (as described herein). Said TSPO modulating agent may modulate TSPO directly or indirectly. Typically TSPO modulating agents of the invention directly modulate TSPO. Preferably said direct TSPO modulating agents are TSPO binding members as described herein.

The term "treat" or "treating" as used herein encompasses prophylactic treatment (e.g. to prevent onset of PEC dysfunction or an associated disease or disorder) as well as corrective treatment (treatment of an individual already suffering from PEC dysfunction or an associated disease or disorder). Preferably, the term "treat" or "treating" as used herein means corrective treatment. The term "treat" or "treating" encompasses treating both PEC dysfunction, symptoms thereof and diseases/disorder associated therewith. In some embodiments the term "treat" or "treating" refers to a symptom of PEC dysfunction.

The "treatment" may be defined as providing a treatment outcome as defined herein, or any combination thereof.

A TSPO modulating agent (e.g. a TSPO binding member), vector, composition or drug delivery system of the invention may be used in the treatment of an individual having PEC dysfunction as described herein. An individual may be screened for PEC dysfunction prior to treatment (e.g. using a bronchoalveolar (BAL) lavage sample or tissue biopsy), and may be selected for treatment based on the level of PEC dysfunction (in other words based on the deviation of one or more PEC phenotype from the normal value in a healthy individual, as described herein).

A "therapeutically effective amount" is any amount of a TSPO modulating agent (e.g. a TSPO binding member), vector, composition or drug delivery system of the invention which, when administered alone or in combination to a patient for treating PEC dysfunction (or preventing further dysfunction) or a symptom thereof or a disease associated therewith is sufficient to provide such treatment of the PEC dysfunction, or symptom thereof, or associated disease. A "prophylactically effective amount" is any amount of a TSPO agent (e.g. TSPO binding member), vector, composition or drug delivery system of the invention that, when administered alone or in combination to an individual inhibits or delays the onset or reoccurrence of PEC dysfunction, or a symptom thereof or disease associated therewith). The prophylactically effective amount may prevent the onset or reoccurrence of PEC dysfunction entirely. "Inhibiting" the onset means either lessening the likelihood of PEC dysfunction onset (or symptom thereof or disease associated therewith) or preventing the onset entirely.

Treating PEC dysfunction may allow associated conditions such as PAH (e.g. IPAH) to be treated earlier in their progression than using conventional treatments, and this prevent or reduce phenotypes associated with PEC dysfunction, or other symptoms and/or pathological changes associated with PEC dysfunction or associated diseases, such as pulmonary vascular remodelling. Thus, compared with conventional treatments for PH, treatment according to the invention may prevent or reducing such phenotypes or other symptoms and/or pathological changes.

The terms "subject", "individual" and "patient" are used interchangeably herein to refer to a mammalian individual. Generally, the individual may be human; in other words, in one embodiment, the "individual" is a human. The individual may not have been previously diagnosed as having PEC dysfunction (or symptom thereof or disease associated therewith). Alternatively, the individual may have been previously diagnosed as having PEC dysfunction (or symptom thereof or disease associated therewith). The individual may also be one who exhibits disease risk factors, or one who is asymptomatic for PEC dysfunction (or symptom thereof or disease associated therewith). The individual may also be one who is suffering from or is at risk of developing PEC dysfunction (or symptom thereof or disease associated therewith).

Administration of a TSPO modulating agent of the invention (e.g. a TSPO binding member), vector, composition or drug delivery system of the invention may be by any appropriate route. Non-limiting examples of conventional routes include inhalation; intraperitoneal, intravenous, intraarterial, subcutaneous, and/or intramuscular injection; infusion; rectal, vaginal, topical and oral administration. The most appropriate administration route may be selected based on the TSPO modulating agent of the invention (e.g. a TSPO binding member), vector, composition or drug delivery system to be used. Preferably the TSPO modulating agent (e.g. a TSPO binding member), vector, composition or drug delivery system of the invention may be administered by inhalation, particularly oropharyngeal inhalation and/or nasal inhalation, or by intravenous or intra-arterial administration.

It will be appreciated by one of skill in the art that the appropriate dosage of a TSPO modulating agent (e.g. a TSPO binding member), vector, composition or drug delivery system of the invention, can vary from individual to individual. Determining the optimal dosage will generally involve the balancing of the level of therapeutic benefit against any risk or deleterious side effects. The selected dosage level will depend on a variety of factors including, the route of administration, the severity of the individual's/patient's fibrosis, and the species, sex, age, weight, condition, general health, and prior medical history of the individual/patient. Advantageously, the present inventors have identified suitable dosages of a TSPO modulating agent of the invention, particularly a TSPO binding member such as XBD-173, which provide the PEC dysfunction inhibitory effects claimed. Typically, the TSPO modulating agent of the invention, particularly a TSPO binding member such as XBD-173, is administered at a dose of about 0.1 to 20 mg/kg. Preferably, the TSPO modulating agent of the invention, particularly a TSPO binding member such as XBD-173, is administered at a dose of about 0.1 to 10 mg/kg, even more preferably at dose of about 1 to 10 mg/kg, even more preferably at a dose of about 1 to 5 mg/kg. In a particularly preferred embodiment, XBD-173 is administered at a dose of about 1 to 10 mg/kg or 1 to 5 mg/kg by oral administration. This particularly preferred dose may be administered daily (once a day) and may be administered indefinitely.

The frequency of dosing selected may also be dependent on a range of factors. The skilled person will be able to select the most suitable dosing regimen appropriate for the individual. Typically, a TSPO modulating agent (particularly a TSPO binding member such as XBD-173), vector, composition or drug delivery system of the invention is administered between about once every three months to about four times per day. For example, the TSPO modulating agent (particularly a TSPO binding member such as XBD-173), vector, composition or drug delivery system of the invention may be administered once every three months, once per month, twice per month, once per week, twice per week, 3 times per week, 4 times per week, 5 times per week, 6 times per week, once a day, twice a day, 3 times per day, 4 times per day or more. Preferably, the TSPO modulating agent (particularly a TSPO binding member such as XBD-173), vector, composition or drug delivery system of the invention is administered about once per day. Treatment may be continued for at least one month, at least two months, at least four months, at least six months, at least one year, at least two years, at least five years, at least ten years or more, including indefinite treatment/treatment for the life of an individual.

A TSPO modulating agent (particularly a TSPO binding member such as XBD-173), vector, composition or drug delivery system of the invention may have a treatment outcome as defined herein within 8-52 weeks (preferably within 36 weeks, more preferably within 24 weeks, even more preferably within 12 weeks) from baseline. Preferably, administration of the TSPO modulating agent (particularly a TSPO binding member such as XBD-173), vector, composition or drug delivery system of the invention may provide a treatment outcome within 36 weeks, more preferably within 24 weeks, even more preferably within 12 weeks.

The treatment outcome may be sustained (e.g. maintained) subsequent to and/or during treatment for several weeks or months or years. A TSPO modulating agent (particularly a TSPO binding member such as XBD-173), vector, composition or drug delivery system of the invention may provide a sustained treatment outcome for at least 5, 10, 12, 16, 18, 20, 22, 24, 38, 32, 36, 40, 52, 78 or 104 weeks. For example, administration of a TSPO modulating agent (particularly a TSPO binding member such as XBD-173), vector, composition or drug delivery system of the invention may provide a sustained treatment outcome for at least 5 weeks, at least 10 weeks, at least 20 weeks, or at least 52 weeks.

A TSPO modulating agent (particularly a TSPO binding member such as XBD-173), vector, composition or drug delivery system of the invention may be used in combination with one or more additional active ingredient or therapeutic, such as an agent which relaxes vascular tone and/or an anti-inflammatory. By way of non-limiting example, the TSPO modulating agent (particularly a TSPO binding member such as XBD-173), vector, composition or drug delivery system of the invention may be used in combination with PDE5 inhibitors, ERA, prostacyclin and/or a NO stimulator, e.g. sildenafil, tadalafil, macetentan, epoprostinil, selexipag, riociguat.

The one or more additional active ingredient or therapeutic may be administered sequentially (before or after) the TSPO modulating agent (particularly a TSPO binding member such as XBD-173), vector, composition or drug delivery system of the invention. The one or more additional active ingredient or therapeutic may be administered simultaneously with the TSPO modulating agent (particularly a TSPO binding member such as XBD-173), vector, composition or drug delivery system of the invention.

The invention also provides a TSPO modulator for use in a method of treating a disease or disorder associated with dysfunction of pulmonary endothelial cells. The invention provides a TSPO modulator for use in a method of treating pulmonary hypertension; and/or heart failure. Preferably the invention provides a TSPO modulator for use in a method of treating PAH, optionally IPAH and/or PH-HFpEF.

The invention also provides a method for the treatment or prevention of PEC dysfunction (or symptom thereof or disease associated therewith), comprising administering a TSPO modulating agent (particularly a TSPO binding member such as XBD-173), vector, composition or drug delivery system of the invention.

The invention also provides a TSPO modulating agent (particularly a TSPO binding member such as XBD-173), vector, composition or drug delivery system of the invention for use in the manufacture of a medicament for the treatment or prevention of PEC dysfunction (or symptom thereof or disease associated therewith).

Compositions and Formulations

The invention provides compositions, particularly pharmaceutical compositions, comprising a TSPO modulating agent (particularly a TSPO binding member such as XBD-173), vector, composition or drug delivery system of the invention and a pharmaceutically acceptable excipient, diluent, adjuvant, immunoregulatory agent and/or antimicrobial compound.

The TSPO modulating agent (particularly a TSPO binding member such as XBD-173) may be in the form of a pro-drug, analogue, derivate, salt, hydrate or solvate as described herein.

Compositions or formulations comprising a TSPO modulating agent (particularly a TSPO binding member such as XBD-173), vector, composition or drug delivery system of the invention may further comprise one or more additional active ingredient or therapeutic, such as an agent which relaxes vascular tone and/or an anti-inflammatory as described herein. The TSPO modulating agent (particularly a TSPO binding member such as XBD-173), vector, composition or drug delivery system of the invention and the one or more additional active ingredient or therapeutic may be provided as a kit of parts.

As described herein, administration of immunogenic compositions, therapeutic formulations, medicaments and prophylactic formulations is generally by conventional routes, with inhalation and particularly oropharyngeal inhalation, being preferred.

Formulation of a TSPO modulating agent (particularly a TSPO binding member such as XBD-173), vector, composition or drug delivery system of the invention may therefore be adapted using routine practice to suit the preferred route of administration.

Formulations suitable for distribution as aerosols are preferred, and it would be routine for one of ordinary skill in the art to prepare such formulations.

By way of further non-limiting example, an TSPO modulating agent (particularly a TSPO binding member such as XBD-173), vector, composition or drug delivery system of the invention, compositions or therapeutic/prophylactic formulations and/or medicaments thereof may be prepared as injectables, either as liquid solutions or suspensions. Solid forms suitable for solution in, or suspension in, liquid prior to injection may alternatively be prepared. The preparation may also be emulsified, or the peptide encapsulated in liposomes or microcapsules. The TSPO modulating agent (particularly a TSPO binding member such as XBD-173), vector, composition or drug delivery system of the invention may also be formulated as a dry-powder formulation.

The active immunogenic ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the composition may contain minor amounts of auxiliary substances such as wetting or emulsifying agents, pH buffering agents, and/or adjuvants which enhance the effectiveness of the vaccine.

Generally, the carrier is a pharmaceutically-acceptable carrier. Non-limiting examples of pharmaceutically acceptable carriers include water, saline, and phosphate-buffered saline. In some embodiments, however, the composition is in lyophilized form, in which case it may include a stabilizer, such as BSA. In some embodiments, it may be desirable to formulate the composition with a preservative, such as thiomersal or sodium azide, to facilitate long term storage.

Examples of additional adjuvants which may be effective include but are not limited to: complete Freunds adjuvant (CFA), Incomplete Freunds adjuvant (IFA), Saponin, a purified extract fraction of Saponin such as Quil A, a derivative of Saponin such as QS-21, lipid particles based on Saponin such as ISCOM/ISCOMATRIX, *E. coli* heat labile toxin (LT) mutants such as LTK63 and/or LTK72, aluminium hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(I'-2'-dipalmitoyl-sn-glycero-3-hydroxyphosphoryl oxy)-ethylamine (CGP 19835 A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion, the MF59 formulation developed by Novartis, and the AS02, AS01, AS03 and AS04 adjuvant formulations developed by GSK Biologicals (Rixensart, Belgium).

Examples of buffering agents include, but are not limited to, sodium succinate (pH 6.5), and phosphate buffered saline (PBS; pH 6.5 and 7.5).

Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably I %-2%.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders.

Screening Assays

The present inventors are the first to demonstrate that treating PEC dysfunction by modulating TSPO results in quantifiable phenotypic changes in cells of the pulmonary vasculature, particularly PECs, smooth muscle cells and fibroblasts. Therefore, quantifying these changes in an in vitro setting has the potential to identify other agents which inhibit the PEC dysfunction, and hence have therapeutic potential for the treatment of PEC dysfunction as well as symptoms thereof and diseases associated therewith.

Accordingly, the invention also provides a method for identifying an agent which inhibits PEC dysfunction comprising the steps of: (a) culturing cells in vitro; (b) adding a test agent to the cultured cells; and (c) determining a change in phenotype, for example apoptosis or pro-inflammatory activation, in response to the test agent.

Any type of test agent may be employed in a method of the invention. The skilled person will be familiar with the various types of test agents which may be added to cultured cells in vitro. The test agent may be any type of TSPO modulating agent (e.g. a TSPO binding member) as described herein. By way of non-limiting example, the test agent may be a small molecule, a nucleic acid agent (for example, an siRNA, a plasmid, an antisense oligonucleotide or a nucleic acid aptamer), an antibody or antibody-fragment thereof, or a peptide aptamer. Vectors, compositions or drug delivery systems comprising or expressing a test agent may also be employed in a screening method of the invention. Any disclosure herein in relation to vectors, drug delivery systems and compositions applies equally and without limitation for vectors, drug delivery systems and compositions comprising or expressing test agents for use in a screening method of the invention. By way of non-limiting example, a vector may be an adeno-associated viral vector, an adenoviral vector or a lentiviral vector comprising a nucleic sequence encoding the test agent. By way of a further non-limiting example, a liposomal drug delivery system comprising a test agent may be used.

Any cell type capable of being cultured in vitro may be utilised in a screening method of the invention. Typically, the cells are primary cells (i.e. cells derived from animal tissues) or cell lines. The cells used in a method of the invention may be a cell type involved in PEC dysfunction or an associated disease. By way of non-limiting example, the cells may be PECs or smooth muscle cells or fibroblasts from the pulmonary vasculature.

The cells may be derived from an individual to be treated, i.e. from an individual with PEC dysfunction already occurring. The cells may be derived from a biopsy sample of an individual with PEC dysfunction. Cells, particularly PECs or smooth muscle cells or fibroblasts from the pulmonary vasculature may be isolated from a biopsy sample using flow cytometry.

The phenotype assessed using a screening method of the invention may be any phenotype or combination thereof as described herein in the context of treatment outcomes, for example apoptosis or pro-inflammatory activation. Particularly screening may involve the use of PECs or smooth muscle cells or fibroblasts from the pulmonary vasculature and determining, for example apoptosis or pro-inflammatory activation, of said cells.

The change in phenotype may be compared with a control. Any appropriate control may be used, and it is within the standard competency of one of ordinary skill in the art to select an appropriate control. Examples of suitable controls are described herein. For example, a control may be a population of the same cell type (preferably from the same source), wherein the control cells are cultured in the same conditions as the cells exposed to the test agent, vector, composition or drug delivery system, but wherein the control cells are not exposed to the test agent, vector, composition or drug delivery system.

A screening method of the invention may consist of the steps described herein (carried out in sequentially in the described order), or may comprise additional steps. Non-limiting example of additional steps include isolating and/or the cells after exposure to the test agent, vector, composition or drug delivery system.

Sequence Homology

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22 (22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264 (4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8 (5) CABIOS 501-509 (1992); Gibbs sampling, see, e.g., C. E. Lawrence et al., Detecting Subtle Sequence Signals: A Gibbs Sampling Strategy for Multiple Alignment, 262 (5131) Science 208-214 (1993); Align-M, see, e.g., Ivo Van Walle et al., Align-M—A New Algorithm for Multiple Alignment of Highly Divergent Sequences, 20 (9) Bioinformatics: 1428-1435 (2004).

Thus, percent sequence identity is determined by conventional methods. See, for example, Altschul et al., Bull. Math. Bio. 48: 603-16, 1986 and Henikoff and Henikoff, Proc. Natl. Acad. Sci. USA 89:10915-19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown below (amino acids are indicated by the standard one-letter codes).

The "percent sequence identity" between two or more nucleic acid or amino acid sequences is a function of the number of identical positions shared by the sequences. Thus, % identity may be calculated as the number of identical nucleotides/amino acids divided by the total number of nucleotides/amino acids, multiplied by 100. Calculations of % sequence identity may also take into account the number of gaps, and the length of each gap that needs to be introduced to optimize alignment of two or more sequences. Sequence comparisons and the determination of percent identity between two or more sequences can be carried out using specific mathematical algorithms, such as BLAST, which will be familiar to a skilled person.

ALIGNMENT SCORES FOR DETERMINING SEQUENCE IDENTITY

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |

-continued

ALIGNMENT SCORES FOR DETERMINING SEQUENCE IDENTITY

| | | | | | | | | | | | | | | | | | | | | |
|---|---|---|---|---|---|---|---|---|---|---|---|---|---|---|---|---|---|---|---|---|
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

The percent identity is then calculated as:

$$\frac{\text{Total number of identical matches}}{\left[\begin{array}{c}\text{length of the longer sequence plus the}\\ \text{number of gaps introduced into the longer}\\ \text{sequence in order to align the two sequences}\end{array}\right]}\times 100$$

Substantially homologous polypeptides are characterized as having one or more amino acid substitutions, deletions or additions. These changes are preferably of a minor nature, that is conservative amino acid substitutions (as described herein) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag.

In addition to the 20 standard amino acids, non-standard amino acids (such as 4-hydroxyproline, 6-N-methyl lysine, 2-aminoisobutyric acid, isovaline and α-methyl serine) may be substituted for amino acid residues of the polypeptides of the present invention. A limited number of non-conservative amino acids, amino acids that are not encoded by the genetic code, and unnatural amino acids may be substituted for polypeptide amino acid residues. The polypeptides of the present invention can also comprise non-naturally occurring amino acid residues.

Non-naturally occurring amino acids include, without limitation, trans-3-methylproline, 2,4-methano-proline, cis-4-hydroxyproline, trans-4-hydroxy-proline, N-methylglycine, allo-threonine, methyl-threonine, hydroxy-ethylcysteine, hydroxyethyl homo-cysteine, nitro-glutamine, homoglutamine, pipecolic acid, tert-leucine, norvaline, 2-azaphenylalanine, 3-azaphenyl-alanine, 4-azaphenyl-alanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell free system comprising an *E. coli* S30 extract and commercially available enzymes and other reagents. Proteins are purified by chromatography. See, for example, Robertson et al., J. Am. Chem. Soc. 113:2722, 1991; Ellman et al., Methods Enzymol. 202:301, 1991; Chung et al., Science 259:806-9, 1993; and Chung et al., Proc. Natl. Acad. Sci. USA 90:10145-9, 1993). In a second method, translation is carried out in *Xenopus oocytes* by microinjection of mutated mRNA and chemically aminoacylated suppressor tRNAs (Turcatti et al., J. Biol. Chem. 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. See, Koide et al., Biochem. 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395-403, 1993).

A limited number of non-conservative amino acids, amino acids that are not encoded by the genetic code, non-naturally occurring amino acids, and unnatural amino acids may be substituted for amino acid residues of polypeptides of the present invention.

Essential amino acids in the polypeptides of the present invention can be identified according to procedures known in the art, such as site-directed mutagenesis or alanine-scanning mutagenesis (Cunningham and Wells, Science 244: 1081-5, 1989). Sites of biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306-12, 1992; Smith et al., J. Mol. Biol. 224:899-904, 1992; Wlodaver et al., FEBS Lett. 309:59-64, 1992. The identities of essential amino acids can also be inferred from analysis of homologies with related components (e.g. the translocation or protease components) of the polypeptides of the present invention.

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

SEQUENCE INFORMATION

```
SEQ ID NO: 1-Homo sapiens TSPO amino acid sequence
MAPPWVPAMG FTLAPSLGCF VGSRFVHGEG LRWYAGLQKP SWHPPHWVLG PVWGTLYSAM GYGSYLVWKE
LGGFTEKAVV PLGLYTGQLA LNWAWPPIFF GARQMGWALV DLLLVSGAAA ATTVAWYQVS PLAARLLYPY
LAWLAFTTTL NYCVWRDNHG WRGGRRLPE

SEQ ID NO: 2-Homo sapiens TSPO mRNA sequence
aactcctgcc aggcagtgcc cttcccggag cgtgccctcg ccgctgagct cccctgaaca gcagctgcag
cagccatggc cccgccctgg gtgcccgcca tgggcttcac gctggcgccc agcctggggt gcttcgtggg
ctcccgcttt gtccacggcg agggtctccg ctggtacgcc ggcctgcaga agccctcgtg gcacccgccc
cactgggtgc tgggccctgt ctggggcacg ctctactcag ccatggggta cggctcctac ctggtctgga
aagagctggg aggcttcaca gagaaggctg tggttcccct gggcctctac actgggcagc tggccctgaa
ctgggcatgg ccccccatct tctttggtgc ccgacaaatg ggctgggcct tggtggatct cctgctggtc
agtggggcgg cggcagccac taccgtggcc tggtaccagg tgagcccgct ggccgcccgc ctgctctacc
cctacctggc ctggctggcc ttcacgacca cactcaacta ctgcgtatgg cgggacaacc atggctggcg
tgggggacgg cggctgccag agtgagtgcc cggcccacca gggactgcag ctgcaccagc aggtgccatc
acgcttgtga tgtggtggcc gtcacgcttt catgaccact gggcctgcta gtctgtcagg gccttggccc
aggggtcagc agagcttcag aggtggcccc acctgagccc ccacccggga gcagtgtcct gtgctttctg
catgcttaga gcatgttctt ggaacatgga attttataag ctgaataaag tttttgactt ccttta
```

EXAMPLES

The invention will be further clarified by the following examples, which are intended to be purely exemplary of the invention and are in no way limiting.

Example 1—Target Validation of TSPO

PBR28 (Imanova Ltd.) is a radioligand for TSPO. Monocrotaline (MCT) induces PH in a rat model.

PET imaging was performed in healthy control and MCT 4 weeks rats (60 mg/kg subcutaneous injection). The uptake of TSPO PET tracer, $^{11}$C-PBR28, was measured in the lungs and RV. Ligand specificity binding was tested in rats treated with XBD-173 prior to PET imaging.

As shown in FIG. 1, PBR28 uptake was significantly increased in the MCT rat lungs compared to control. A two-fold increase of the rate constant k3 represents the increased receptor biding. XBD-173 blocked PBR28 lung signals, confirming the radioligand specificity. These results were consistent with histological examination of MCT rat and Western blotting, which demonstrated significantly increased expression of TSPO in the MCT lungs in comparison to controls.

Figure 2:
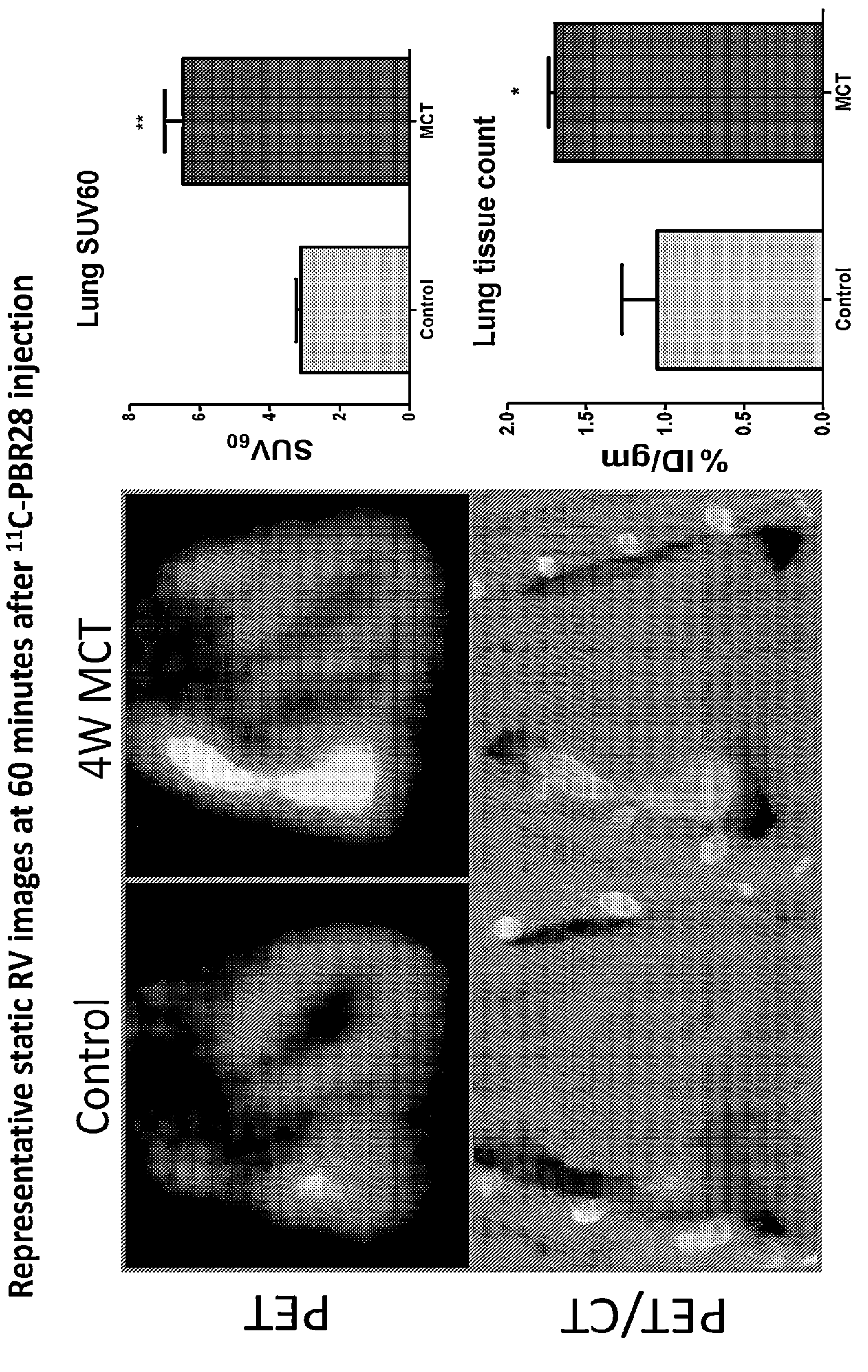
FIG. 2: PBR28 uptake in the right ventricle (RV). Representative static images (PET/CT co-registered) of the heart from dynamically acquired PET for 60 minutes after $^{11}$C-PBR28 injection and bar charts of $^{11}$C-PBR28 RV uptake expressed as standard uptake value (SUV) and RV percentage of injected dose, (% ID), showing the significantly increased PBR28 uptake in the MCT rat RV compared to control. *$p<0.05$, **$p<0.01$ compared with control.

A significant increase in PBR28 uptake was also observed in the right ventricle (RV) of the MCT rat compared with the control (FIG. 2).

Figure 3:
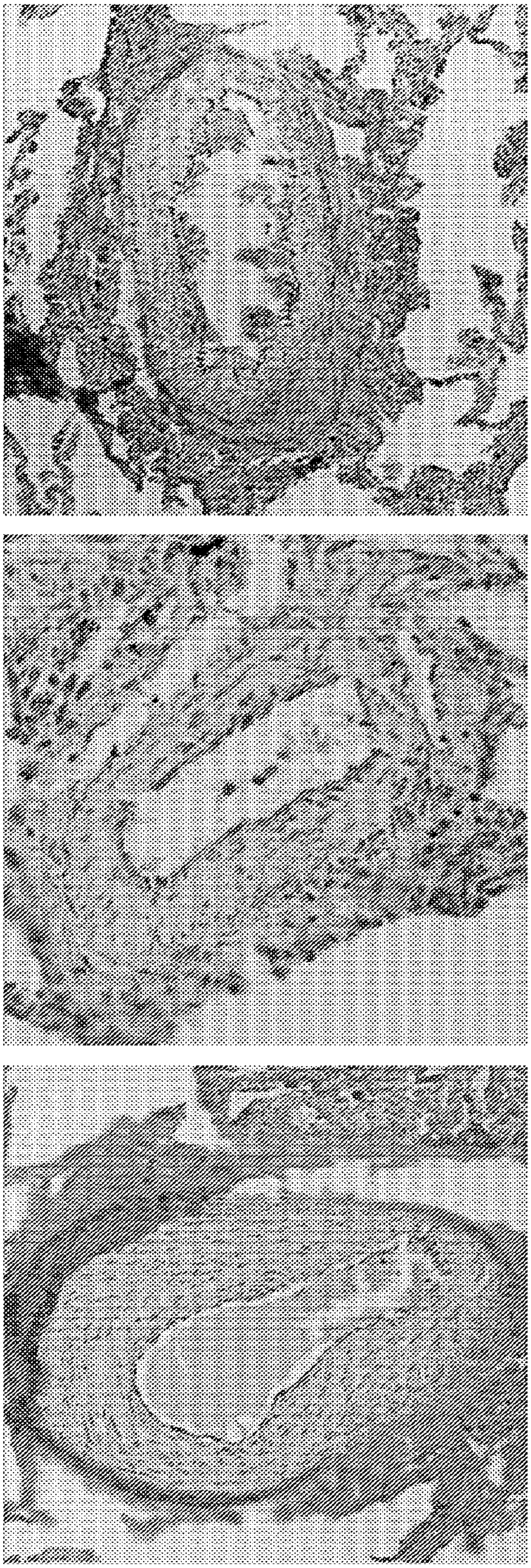
FIG. 3: Immunohistochemistry of TSPO in the pulmonary vessels of IPAH patients. Immunostaining of the lung sections from idiopathic PAH patients indicated TSPO localisation in the remodelled vessels in IPAH patient lungs.

Immunohistochemistry data also indicated TSPO localisation in the remodelled vessels in the lungs of patients with IPAH (FIG. 3).

Example 2—Modulation of TSPO Attenuates Phenotypes Associated with PEC Dysfunction In Vivo Modulation of TSPO by XBD-173 was assessed in MCT rats. In particular, the efficacy of XBD-173 (2 mg/Kg once and twice a day) in MCT rat (treatment from 2-weeks to 4-weeks) was assessed by measuring pulmonary arterial pressure (PAP), right ventricular hypertrophy (RVH), pulmonary vascular remodelling (% of muscularised vessels), and CD68$^+$ macrophage infiltration. Heart and lung glucose metabolism were also assessed by FDG-PET imaging.

Figure 4:
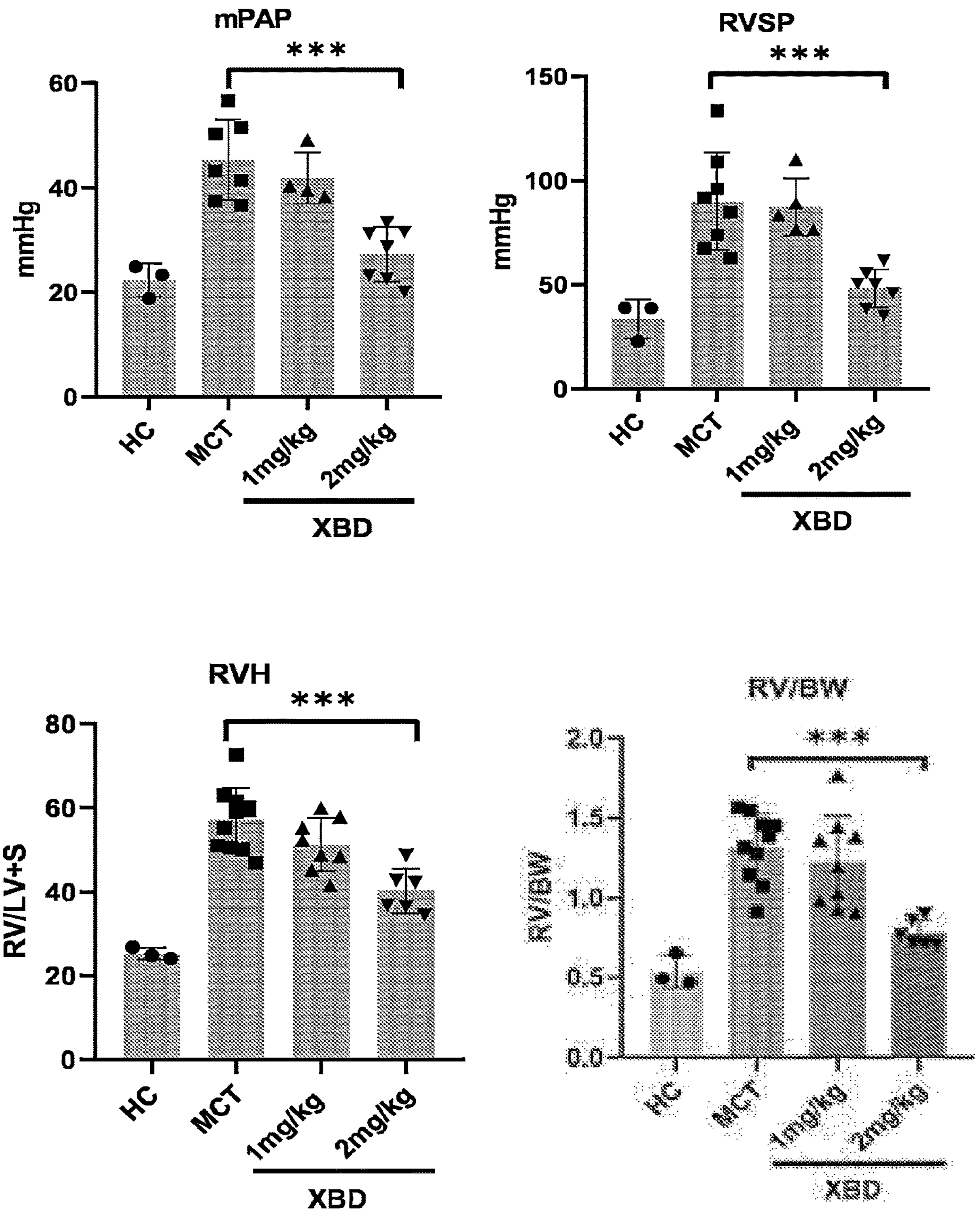
FIG. 4: Effect of XBD-173 on pulmonary arterial pressure, RV systolic pressure and RV hypertrophy. Bar charts illustrating effect of XBD-173 on pulmonary arterial pressure (mPAP), RV systolic pressure (RVSP) and RVH (specifically RV/LV+sp ratio) and or RV/body weight (RV/BW). *$p<0.001$

XBD-173 treatment attenuated the increased PAP (27.23 vs 45.37 mmHg, *$p<0.001$) and RVSP (measured by RV catheterisation, *$p<0.001$), RVH (40.30 vs 57.30; measured using dissected heart tissue, RV/LV+sp ratio, *$p<0.001$) and RV/body weight (RV/BW) (*$p<0.001$) associated with PH in the MCT rats (FIG. 4). This attenuation was dose-dependent manner. Whilst the effect on these phenotypes was statistically significant, notably there was no significant effect on the systemic blood pressure. (data not shown).

Figure 5:
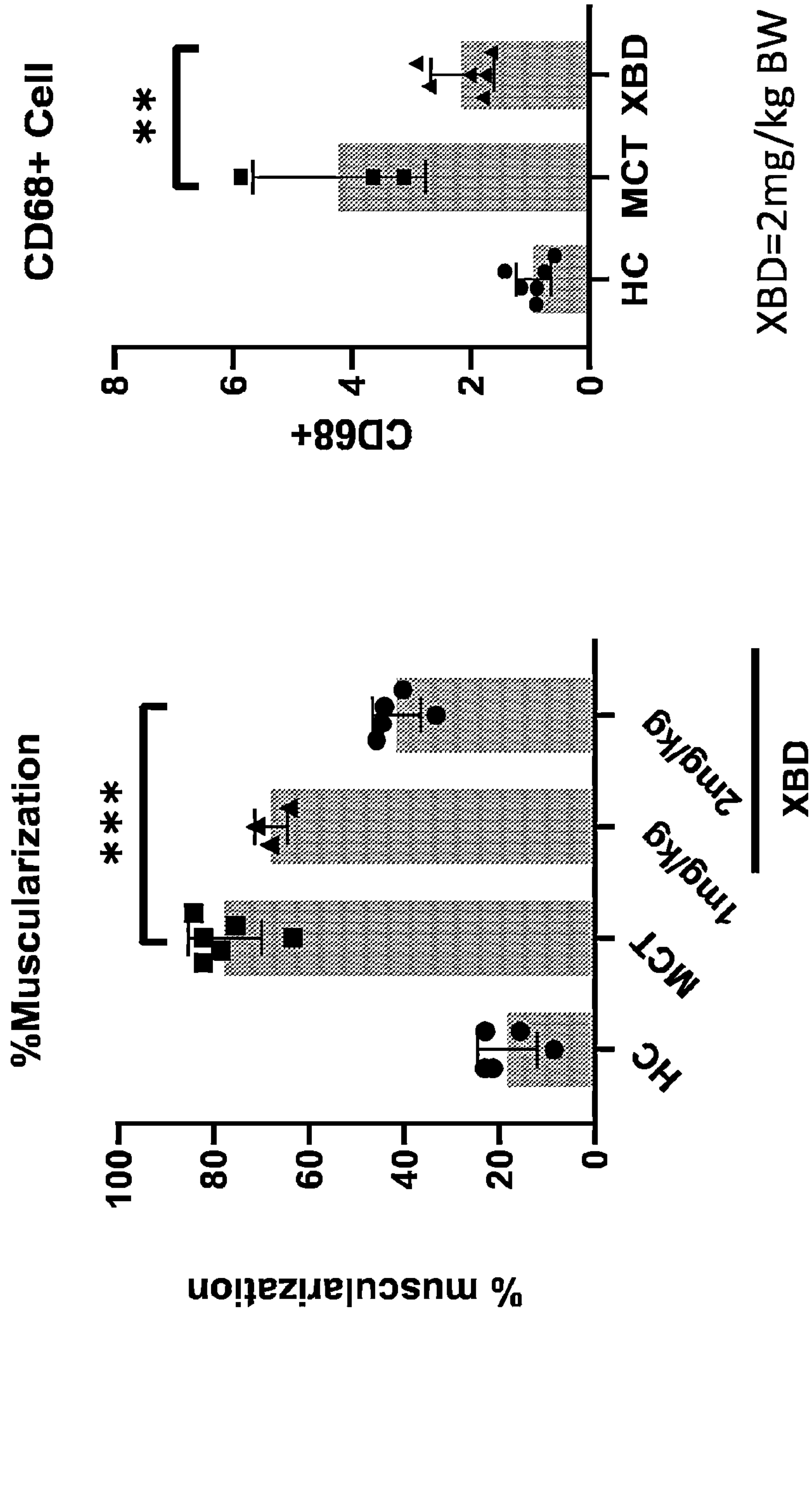
FIG. 5: Effect of XBD-173 on pulmonary vascular remodelling and inflammatory cell infiltration. XBD-173 treatment attenuated pulmonary vascular remodelling (assessed by Van Gieson's elastic staining (EVG) and expressed as % of muscularized vessels of total vessels counts, <100 μM) and inflammatory cell ($CD68^+$, macrophage) infiltration (expressed as the perivascular inflammatory macrophage cells accumulation per $mm^2$). $p<0.001$, *$p<0.001$

XBD-173 treatment also attenuated pulmonary vascular remodelling (53.57 vs 75.24%, $p<0.05$) and inflammatory cell (CD68, macrophage) infiltration (FIG. 5).

Figure 6:
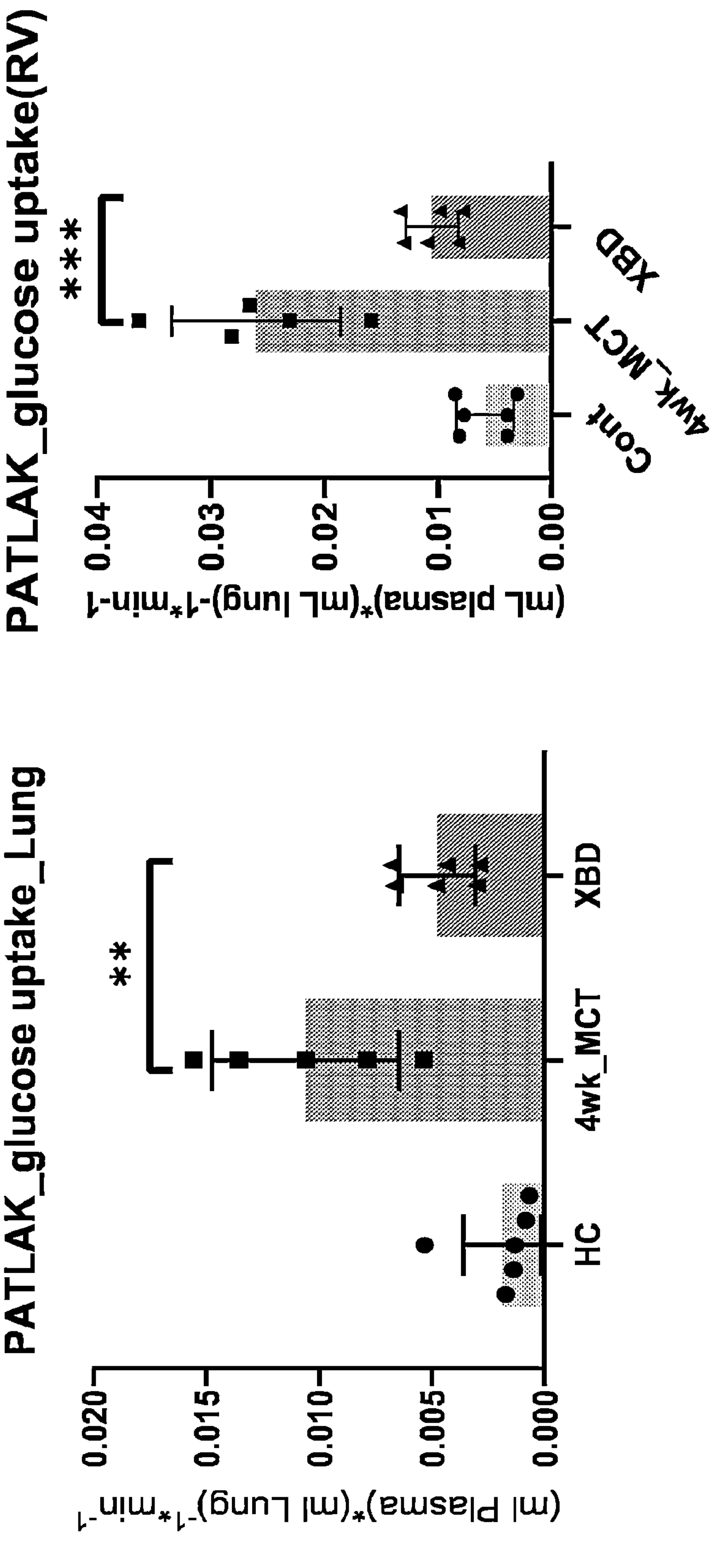
FIG. 6: Effect of XBD-173 on glucose uptake in the lung and RV. XBD-173 treatment attenuated lung and RV FDG uptake (influx rate Ki, measured by $^{18}$FDG tracer with PET/CT). $p<0.001$, ***$p<0.001$

XBD-173 treatment also attenuated lung and RV FDG uptake (influx rate Ki), indicating it modulated cellular metabolic activity (FIG. 6).

Figure 7:
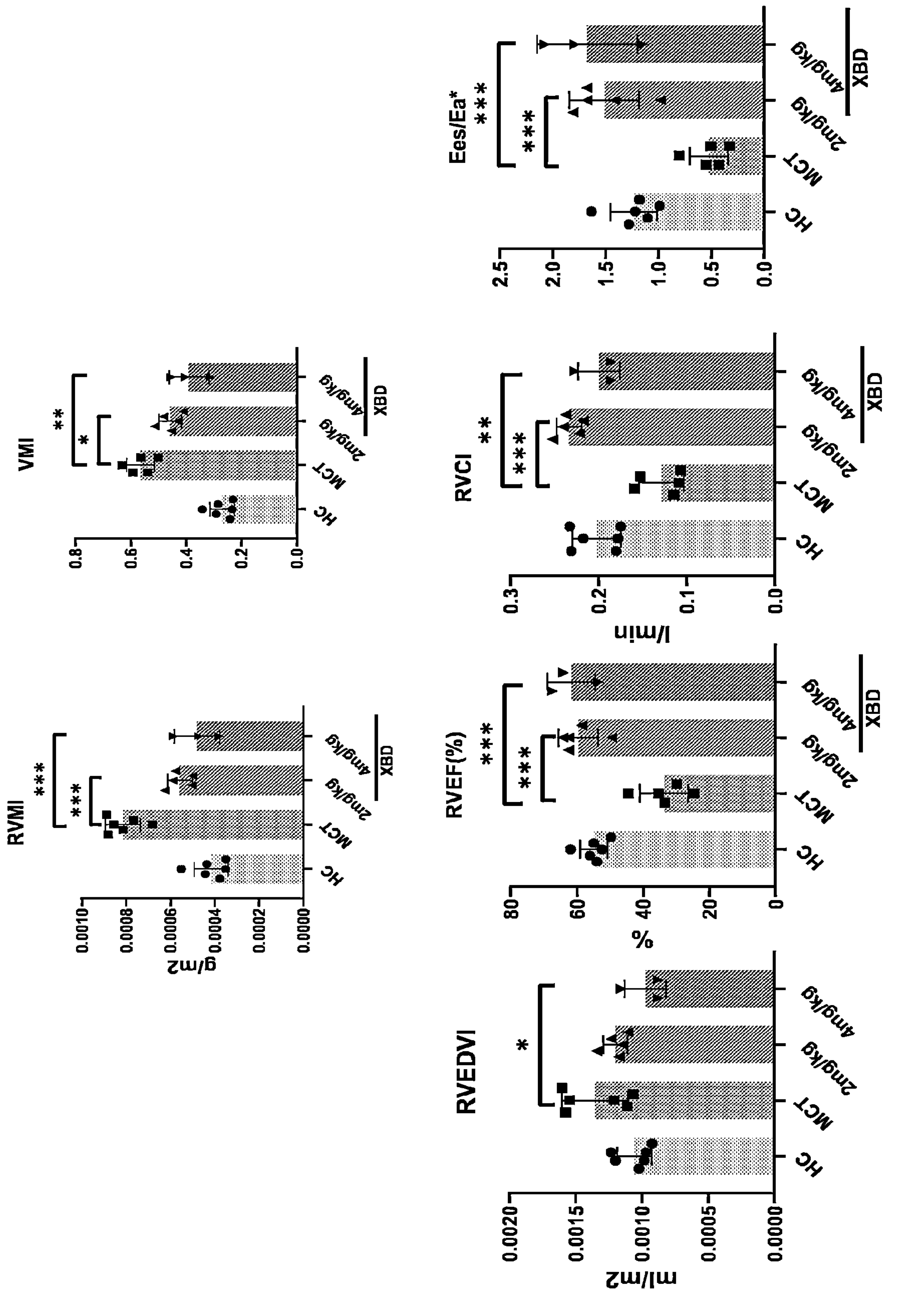
FIG. 7: Effect of XBD-173 on RV structural remodelling and function. Bar charts illustrating the effect of XBD-173 on RV mass index (RVMI), ventricular mass index (VMI), RV ejection fraction (RVEF), RV cardiac index (RVCI), ventricular-vascular coupling (Ees/Ea) and RV end diastolic volume index (RVEDVI). *$P<0.05$, $p<0.001$, *$p<0.001$.

MRI imaging data revealed that XBD-173 treatment reduced RV hypertrophy (expressed as RV mass index (RVMI) and ventricular mass index (VMI)) and improved cardiac function by restoring RV ejection fraction (RVEF), RV cardiac index (RVCI) and ventricular-vascular coupling (Ees/Ea,). At the same time, the treatment significantly reduced the RV dilation (RV end diastolic volume index, (RVEDVI)) (FIG. 7). These data indicated that XBD-173 attenuated RV structural remodelling and improved RV function.

Figure 8:
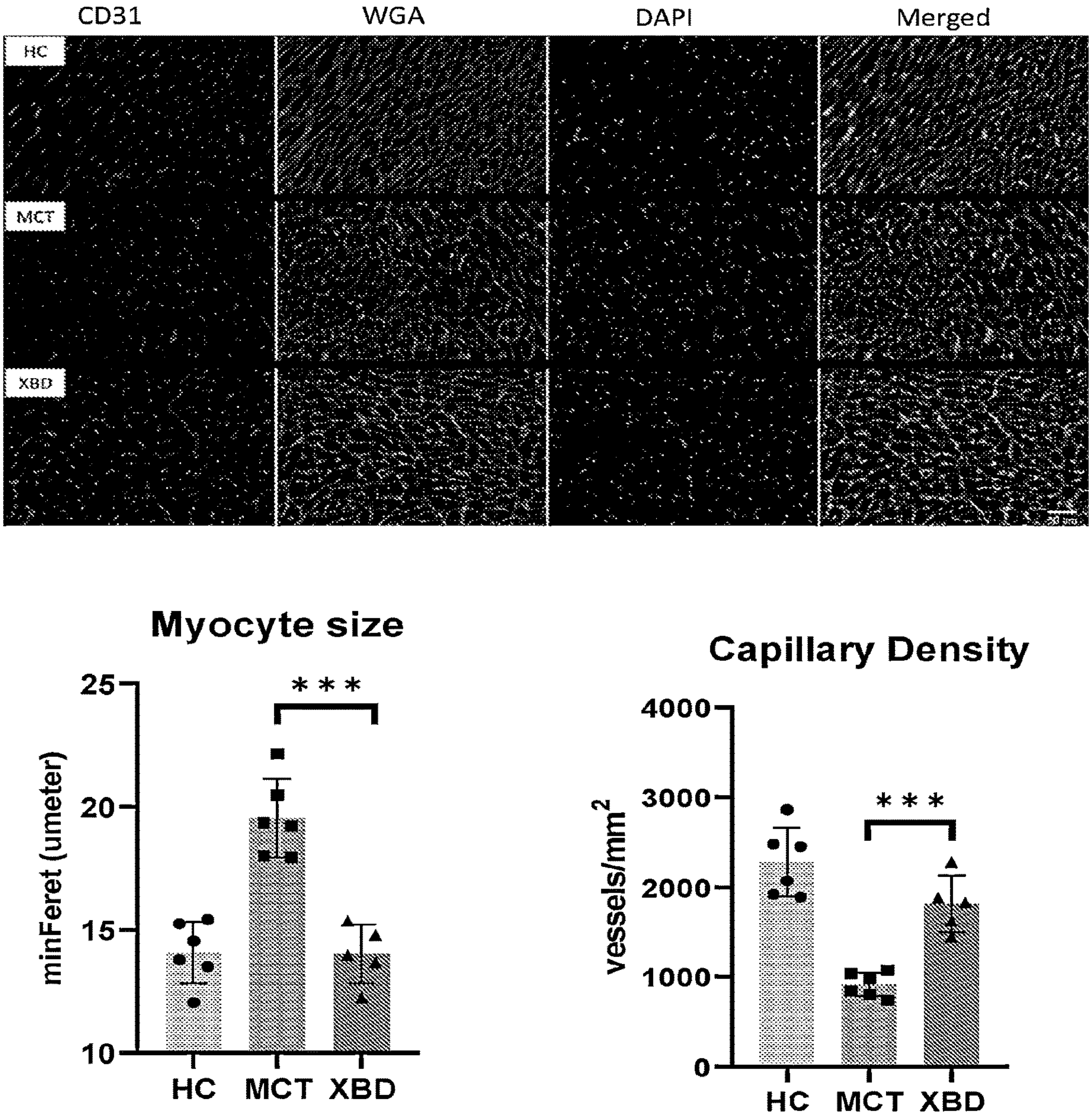
FIG. 8: Effect of XBD-173 on RV cardiomyocyte hypertrophy and capillary density. Immunofluorescence staining of healthy control (HC), MCT rats with/without XBD-173 treatment for cardiomyocyte size (quantified by wheat germ agglutinin (WGA)) and the number of micro-vessels (CD31). Bar charts illustrating the quantitative data from immunofluorescence staining. ***$p<0.001$.

As shown in FIG. 8, XBD-173 treatment also attenuated RV cardiomyocytes hypertrophy and increased capillary density (or prevented rarefaction). Immunofluorescence staining was used to examine the RV structural changes. The cardiomyocyte size was quantified by wheat germ agglutinin (WGA) and the number of micro-vessels by CD31 at RV insertion point. The myocyte size significantly increased in hypertrophied RV of MCT rats, XBD-173 treatment attenuated myocyte size. A decreased capillary density indicated impaired angiogenesis in MCT rats while XBD-173 treatment protected the RV from capillary rarefaction.

Figure 9:
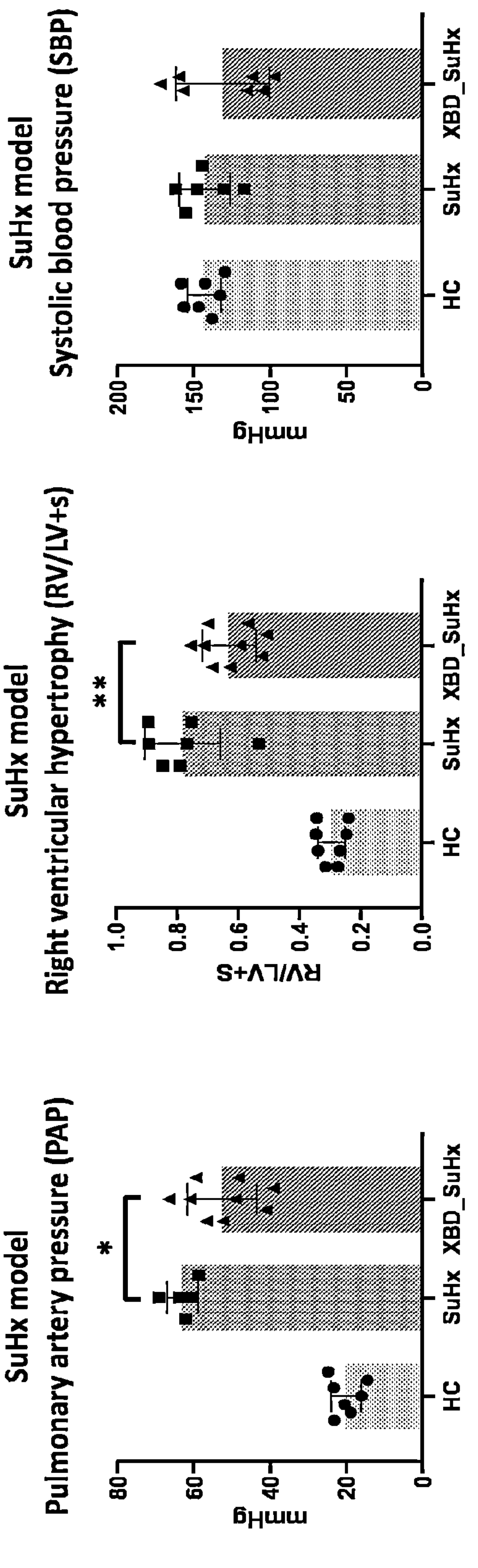
FIG. 9: Effect of XBD-173 treatment on pulmonary arterial pressure (PAP), right ventricular (RV) hypertrophy and systolic blood pressure (SBP). Bar charts illustrating PAP, RV hypertrophy and SBP in healthy controls (HC), Sugen hypoxia (SuHx) rats and SuHx rats following XBD-173 treatment (at 2 mg/Kg twice a day for two weeks). *$P<0.01$,**$P<0.001$.

Example 3—XBD-173 Attenuates the Pulmonary Arterial Pressure and Right Ventricular Hypertrophy Observed in the SuHx Rat The effects of XBD-173 on pulmonary arterial pressure (PAP), right ventricular (RV) hypertrophy and systolic blood pressure were determined in the SuHx rat (a well-established rat model of human pulmonary arterial hypertension). Established pulmonary hypertensive SuHx rats receiving 2 mg/kg XBD-173 twice a day for two weeks showed a significant decrease in PAP and RV hypertrophy (FIG. 9). XBD-173 had no significant effect on the systemic blood pressure in SuHx rats.

Figure 10:
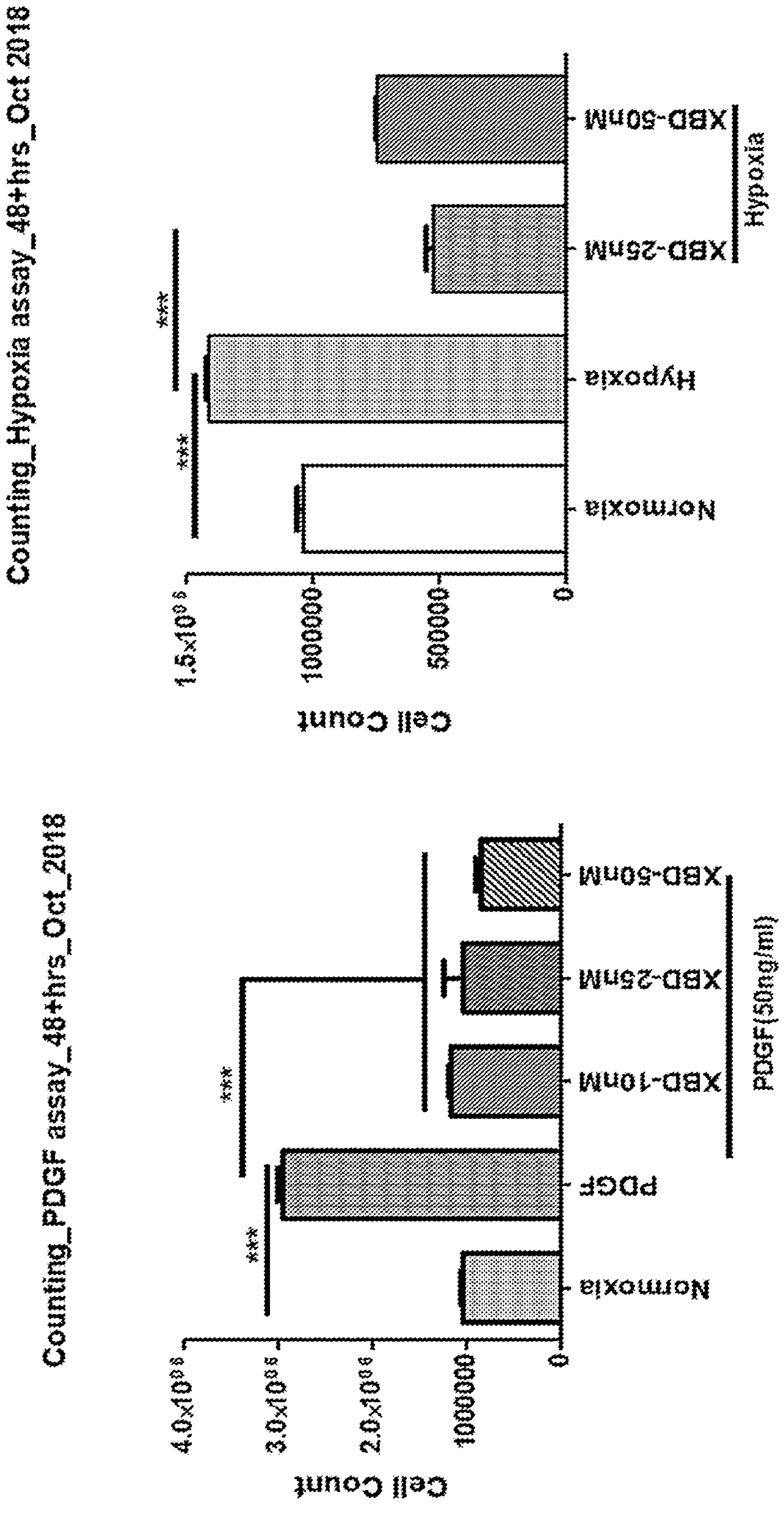
FIG. 10: Effect of XBD-173 on PDGF and hypoxia-stimulated proliferation of human pulmonary arterial smooth muscle cells (PASMCs). Bar charts illustrating the effect of XBD-173 on PDGF- and hypoxia-induced proliferation of PASMCs. ***$p<0.001$.

Example 4—XBD-173 Inhibits Pulmonary Cell Proliferation and Apoptosis In Vitro Human pulmonary artery smooth muscle cells (PASMCs, Lonza) were used for assessing the antiproliferative effects of XBD-173 under platelet derived growth factor (PDGF) and hypoxia stimulus ($O_2$=2%). XBD-173 attenuated PDGF and hypoxia-stimulated proliferation of PASMCs (FIG. 10).

Figure 11:
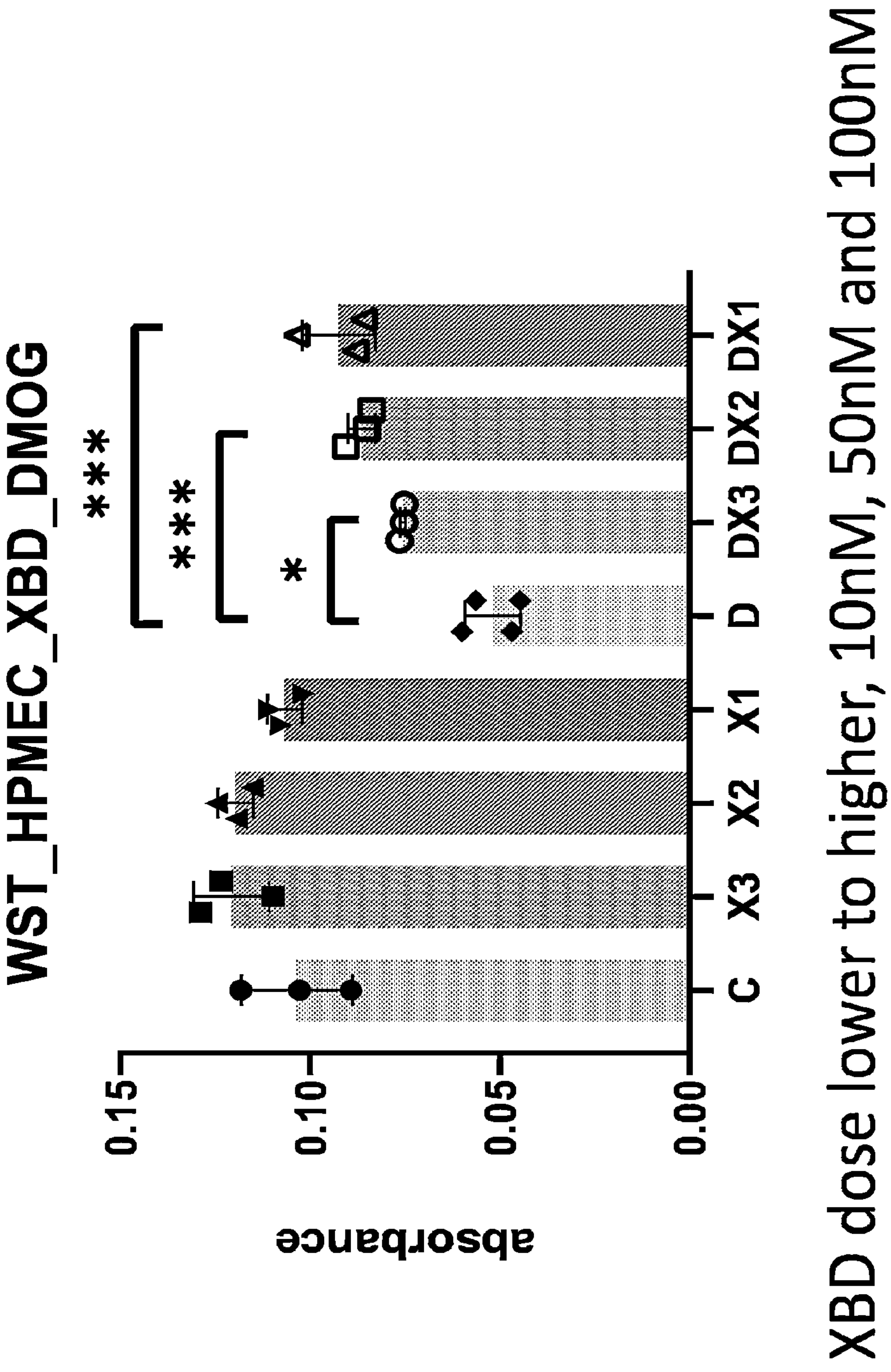
FIG. 11: Effect of XBD-173 on DMOG-induced apoptosis of human pulmonary microvascular endothelial cell (HPMECs). Bar charts illustrating the effect of XBD-173 on DMOG-induced apoptosis of HPMECs. *$P<0.05$, ***$p<0.001$.

The effects of XBD-173 on immortalised human pulmonary microvascular endothelial cells (HPMEC) under DMOG (a permeable prolyl-4-hydroxylase inhibitor which upregulates hypoxia-inducible factor and causes apoptosis) stimulation were also investigated. XBD-173 reversed DMOG-induced apoptotic effects in HPMECs (FIG. 11).

Example 5—TSPO Ligands Attenuated DMOG-induced Apoptosis in HPMEC In Vitro

Figure 12:
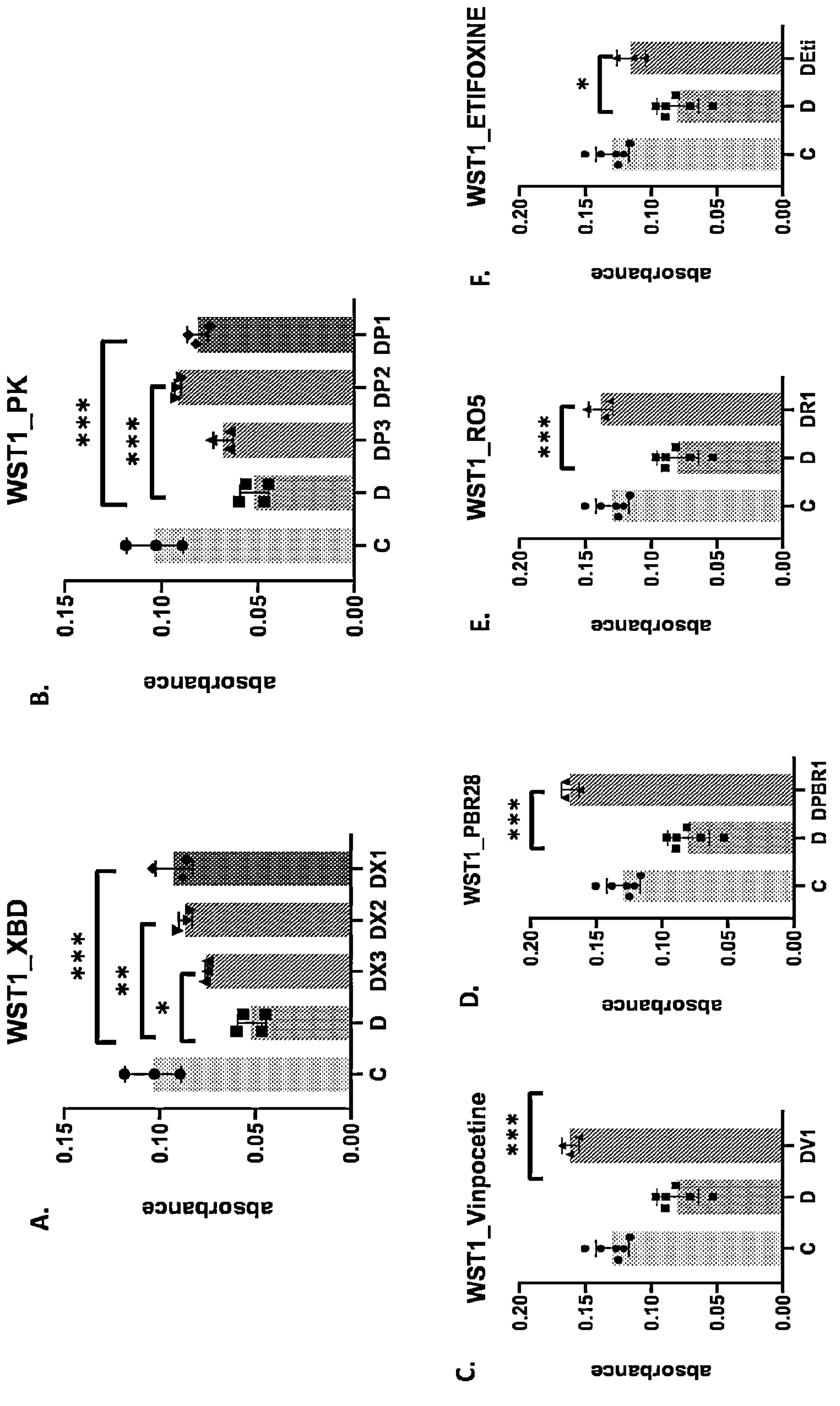
FIG. 12: TSPO ligands attenuated DMOG-induced apoptosis in HPMEC in vitro: (A) XBD-173 at doses of 10 nM (DX3), 50 nM (DX2) and 100 nM (DX1); (B) PK95111 at doses of 3 nM (DP3), 30 nM (DP2) and 300 nM (DP1); (C) Vinpocetine at 800 nM (DV1); (D) PBR28 at 5 nM (DPBR1); (E) Ro 5-4864 at 10 nM (DR1); and (F) Etifoxine at 10 uM (DEti).

The effects of various TSPO ligands on HPMEC under DMOG (a permeable prolyl-4-hydroxylase inhibitor which upregulates hypoxia-inducible factor and causes apoptosis) stimulation were investigated. As shown in FIG. 12, XBD-173, PK95111, Vinpocetine, PBR28, Ro 5-4864, and Etifoxine all reversed DMOG-induced apoptotic effects in HPMECs.

Figure 13:
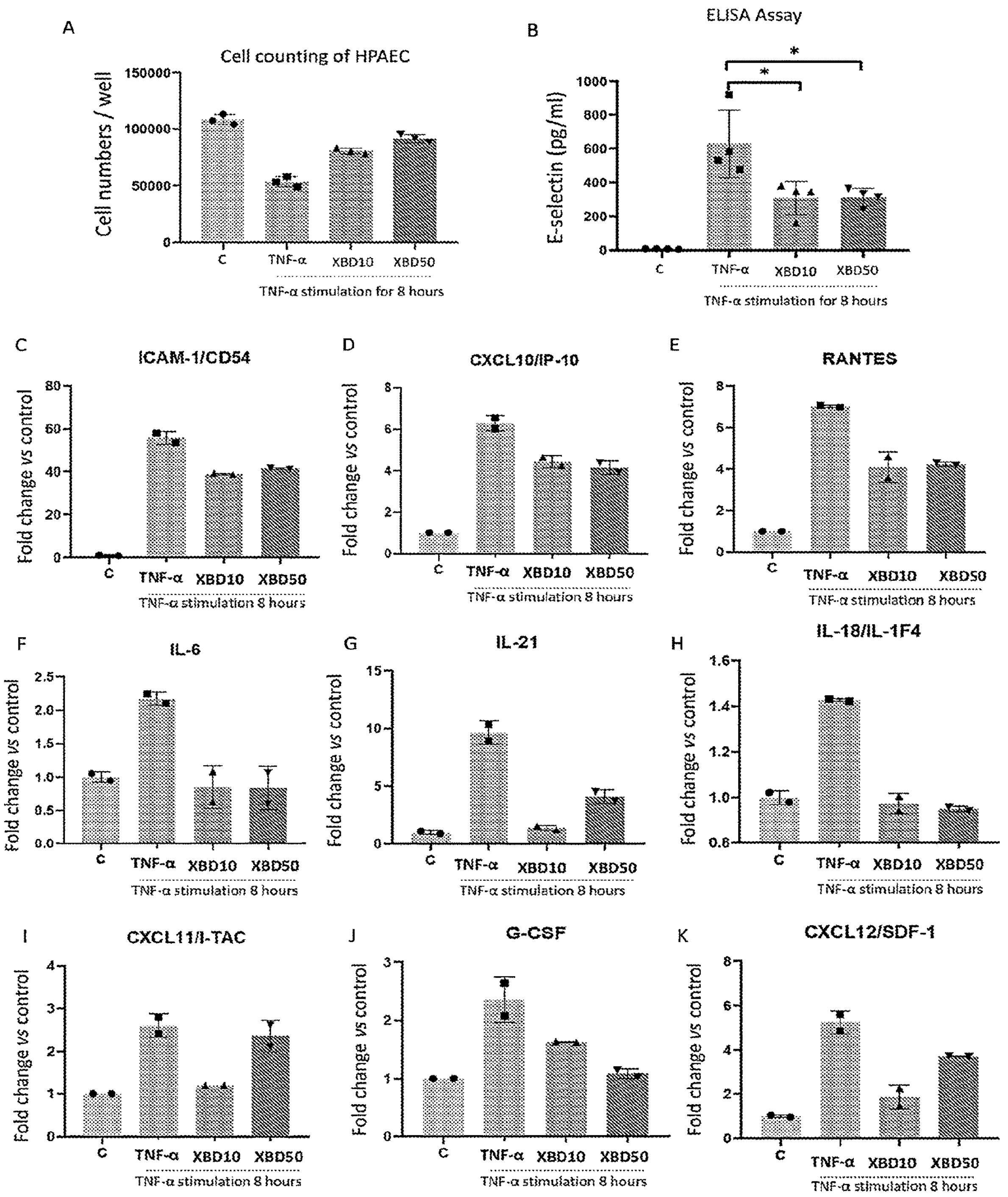
FIG. 13: TSPO ligand XBD173 attenuated cytokine and chemokine release from pulmonary endothelia cell (HPAEC) in response to TNF-α stimulation. (A) number of HPAEC; (B) HPAEC activation quantified using E-selectin expression; (C) ICAM1—expression by HPAEC; (D) CXCL10 secretion; (E) RANTES secretion; (F) IL-6 secretion; (G) IL-21 secretion; (H) IL-18 secretion; (I) CXCIL11 secretion; (J) G-CSF secretion; and (K) CXCL12 secretion; following TNF-α treatment with/without XBD173 (10 nM and 50 nM)

Example 6—TSPO Ligands Attenuated the Pro-inflammatory Effects of TNF-α Stimulation in Human Pulmonary Endothelial Cells (HPAECs) In Vitro HPAECs were pre-treated with XBD173 (10 nM and 50 nM) for 24 hours before TNF-α (10 ng/ml) stimulation for 8 hours. At the end of the experiment, cell numbers were counted and cell culture supernatants collected (n=4 per group, control, TNF-α, TNF-α with XBD 10 nM and 50 nM treatments) for cytokine assay using the proteome profiler human cytokine array kit (R&D systems, ARY005B) and E-selectin ELISA assay. As shown in FIG. 13, XBD173 significantly ($P<0.05$) reduced the activation of HPAECs by TNF-α (demonstrated by the reduction in E-selectin expression following XBD173 treatment). Further, XBD173 observably attenuated release of multiple cytokines and chemokines (CXCL-10, RANTES, IL-6, IL-21, IL-18, CXCL11, G-CSF and CXCL12) from HPAEC in response to TNF-α stimulation.

Figure 14:
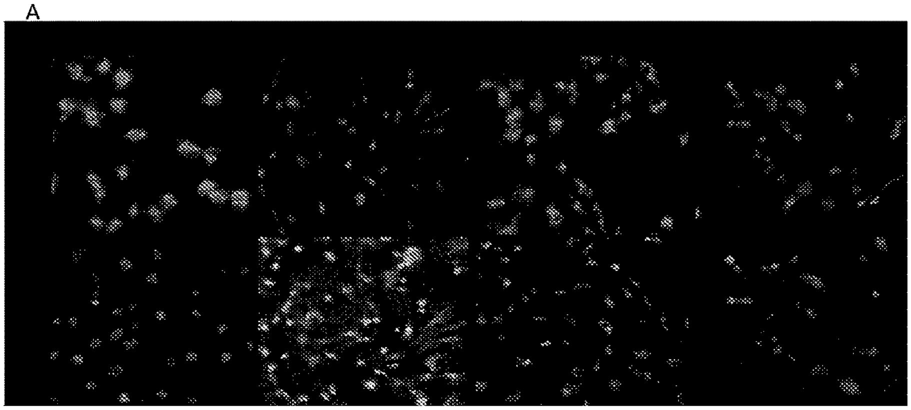
FIG. 14: TSPO ligand XBD173 attenuated TNF-α stimulated Reactive oxygen species (ROS) production and recovered decreased mitochondrial membrane potential in pulmonary endothelia cell (HPAEC). (A) micrographs showing cells stained with TMRE to visualise mitochondrial membrane potential (top panel) and ROS (bottom panel); (B) graph quantifying ROS production; and (C) graph quantifying mitochondrial membrane potential; following TNF-α treatment of HPAEC with/without XBD173 (10 nM and 50 nM)
Figure 14:
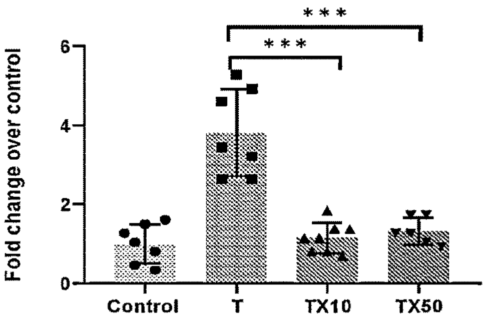
Figure 14:
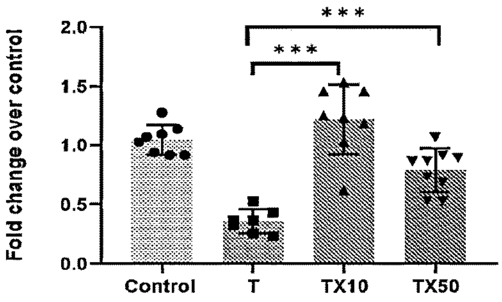

Mitochondrial membrane potential was determined using 20 nM Tetramethylrhodamine, Ethyl Ester, Perchlorate (TMRE; Life technologies, T669). ROS production was detected using 5 uM CellROX Green (Life technologies, C10444). 1 ug/mL Hoechst 33342 (Life technologies, H1399) was added for nucleus staining. Images were obtained with a Zeiss Axio Observer inverted widefield microscope. As shown in FIG. 14, XBD173 signifantly ($P<0.001$) reduced ROS production following TNF-α stimulation, with ROS levels similar to those in the TNF-α untreated control being observed. In addition, XBD173 signifantly ($P<0.001$) increased the mitochondrial membrane potentials following TNF-α stimulation, with the mitochondrial membrane potentials with XBD173 treatment recovering to similar levels to those seen for the TNF-α untreated control.

The invention claimed is:

1. A method for treating or preventing pulmonary endothelial cell (PEC) dysfunction, the method comprising administering a therapeutically effective amount of a translocator protein (TSPO) modulator.

2. The method of claim 1, wherein the TSPO modulator inhibits pro-inflammatory activation of pulmonary endothelial cells.

3. The method of claim 2, wherein inhibition of pro-inflammatory activation of pulmonary endothelial cells comprises:

(a) reducing or attenuating an increase in expression of E-selectin, ICAM1 and/or VCAM1; and/or (b) reducing the level of one or more pro-inflammatory mediator, wherein optionally said one or more pro-inflammatory mediator is selected from IFN-gamma; IL1, 2, 6, 8, 10,17, 18, 21; IP10; I-TAC; G-CSF; MCP-1; PAI1, TNF-alpha, RANTES and/or SDF-1.

4. The method of claim 1, wherein the TSPO modulator:

(a) reduces or attenuates an increase in pulmonary endothelial cell apoptosis;

(b) reduces or attenuates an increase in reactive oxygen species (ROS) production;

(c) reduces or attenuates an increase in vascular tone;

(d) reverses the active metabolic changes seen in pulmonary endothelial cell dysfunction;

(e) increases or attenuates a decrease in anticoagulant properties;

(f) increases or attenuates a decrease in vascular tubule formation;

(g) increases or attenuates a decrease in vascular repair;

(h) reduces or attenuates an increase in disordered pulmonary endothelial cell proliferation and associated neoangiogenesis;

(i) increases or attenuates a decrease in mitochondrial membrane potential; and/or (j) reduces or attenuates an increase in expression of markers of endothelial to mesenchymal transition.

5. The method of claim 4, wherein the TSPO modulator reduces hypoxia-induced pulmonary endothelial cell proliferation by at least 30%, preferably at least 40%.

6. The method of claim 1, wherein the TSPO modulator:

(a) reduces or attenuates an increase in pulmonary arterial pressure;

(b) reduces or attenuates an increase in pulmonary vascular remodelling;

(c) reduces or attenuates an increase in infiltration of inflammatory cells, particularly CD68+ cells, into the lungs; and/or (d) reduces or attenuates an increase in glucose uptake in the lung.

7. The method of claim 6, wherein the TSPO modulator reduces pulmonary arterial pressure by at least 30%.

8. The method of claim 6, wherein pulmonary vascular remodelling corresponds with the percentage of smooth muscle cells within the pulmonary vasculature, and wherein optionally the TSPO modulator reduces the percentage of smooth muscle cells within the pulmonary vasculature by at least 30%.

9. The method of claim 6, wherein the TSPO modulator reduces the infiltration of inflammatory cells, particularly CD68+ cells by at least 30%.

10. The method of claim 6, wherein the TSPO modulator reduces glucose uptake by the pulmonary endothelial cells by at least 40%.

11. The method of claim 1, wherein the dysfunction of the pulmonary endothelial cells is associated with:

(a) pulmonary hypertension; and/or (b) heart failure.

12. The method of claim 11, wherein the pulmonary hypertension is pulmonary arterial hypertension (PAH), optionally idiopathic pulmonary arterial hypertension (IPAH).

13. The method of claim 12, wherein the heart failure is heart failure with preserved ejection fraction and associated pulmonary hypertension (PH-HFpEF).

14. The method of claim 11, wherein the TSPO modulator:

(a) reduces or attenuates an increase in right ventricular systolic pressure;

(b) reduces or attenuates an increase in right ventricular hypertrophy, particularly cardiomyocyte hypertrophy in the right ventricle;

(c) reduces or attenuates an increase in glucose uptake in the right ventricle;

(d) reduces or attenuates an increase in remodelling of the right ventricle;

(e) increases capillary density within the cardiac tissue; and/or (f) improves cardiac performance.

15. The method of claim 1, wherein the TSPO modulator has no effect on systemic blood pressure.

16. The method of claim 1, wherein the TSPO modulator is a TSPO binding member.

17. The method of claim 16, wherein the TSPO binding member is selected from a small molecule, an antibody or antigen-binding fragment thereof, a peptide, a peptidomimetic, a nucleic acid or an aptamer.

18. The method of claim 1, wherein the TSPO modulator is a TSPO binding member is selected from XBD-173, ONO-2952, PK11195, PBR28, DPA713, DPA714, Ro 5-4864, FGIN-1-27, diazepam, lorazepam, midazolam, etifoxine, or a derivative or analogue thereof, optionally in the form of a pharmaceutically acceptable salt.

19. The method of claim 1, wherein the TSPO modulator is comprised within a pharmaceutical composition.

20. The method of claim 1, wherein the TSPO modulator is administered by oral administration, intravenous or intraarterial administration or by inhalation.

21. The method of claim 1, wherein the TSPO modulator is the TSPO binding member XBD-173 and the pulmonary endothelial cell dysfunction is associated with pulmonary arterial hypertension, particularly idiopathic pulmonary arterial hypertension.

22. The method of claim 6, wherein the TSPO modulator reduces pulmonary arterial pressure by at least 40%.

23. The method of claim 6, wherein pulmonary vascular remodelling corresponds with the percentage of smooth muscle cells within the pulmonary vasculature by at least 40%.

24. The method of claim 6, wherein the TSPO modulator reduces the infiltration of inflammatory cells, particularly CD68+ cells by at least 40%.

25. The method of claim 6, wherein the TSPO modulator reduces glucose uptake by the pulmonary endothelial cells by at least 50%.

26. The method of claim 16, wherein the TSPO binding member is a small molecule.

* * * * *